US010363277B2

(12) United States Patent
Bonaci et al.

(10) Patent No.: US 10,363,277 B2
(45) Date of Patent: Jul. 30, 2019

(54) SYNTHETIC RHINOCEROS HORN ANALOGUES

(71) Applicant: PEMBIENT, INC., Seattle, WA (US)

(72) Inventors: George A. Bonaci, Seattle, WA (US); Matthew Markus, Seattle, WA (US)

(73) Assignee: Pembient, Inc., Seattle, WA (US)

( * ) Notice: Subject to any disclaimer, the term of this patent is extended or adjusted under 35 U.S.C. 154(b) by 0 days.

(21) Appl. No.: 15/513,885

(22) PCT Filed: Sep. 23, 2015

(86) PCT No.: PCT/US2015/051721
§ 371 (c)(1),
(2) Date: Mar. 23, 2017

(87) PCT Pub. No.: WO2016/049185
PCT Pub. Date: Mar. 31, 2016

(65) Prior Publication Data
US 2017/0281688 A1    Oct. 5, 2017

Related U.S. Application Data

(60) Provisional application No. 62/053,990, filed on Sep. 23, 2014.

(51) Int. Cl.
*A61K 35/36* (2015.01)
*A61K 45/06* (2006.01)
*A61K 47/42* (2017.01)

(52) U.S. Cl.
CPC .............. *A61K 35/36* (2013.01); *A61K 45/06* (2013.01); *A61K 47/42* (2013.01)

(58) Field of Classification Search
None
See application file for complete search history.

(56) References Cited

U.S. PATENT DOCUMENTS

2008/0004423 A1    1/2008  Kelly et al.

OTHER PUBLICATIONS

Mills, Ed., Rhinoceros Horn and Tiger Bone in China: An Investigation of Trade Since The 1993 Ban, pp. 1-60.. (Year: 1997).*
PBS WETA Nature, Rhino Horn Use: Fact vs. Fiction. (Year: 2010).*
Invitation to Pay Additional Fees dated Jan. 12, 2016 for International Application No. PCT/US15/51721.

Sheng-Qing, et al., "Analysis of Rhinoceros Horn and Its Substitutes by IR Spectrometry", retrieved on Feb. 23, 2016 from <<http://www.rhinoresourcecenter.com/pdf_files/132/1324806757.pdf>>, Chinese Journal of Spectroscopy Laboratory, vol. 28, No. 6, 2011, pp. 3186-3189.
Translated the Vietnamese Office Action dated May 23, 2017 for Vietnamese Patent Application No. 1-2017-01068, a counterpart foreign application of U.S. Appl. No. 15/513,885.
Extended European Search Report dated Apr. 25, 2018 for European Patent Application No. 15843406.8, 9 pages.
Erasmus, "The 'Stop Rhino Poaching through Synthetic Rhino Horns' Initiative", posted on Jun. 12, 2014, retrieved from the internet on Jan. 6, 2016 from https://candiceerasmus.wordpress.com/2014/06/12/the-stop-rhino-poaching-through-synthetic-rhino-horns-initiative/.
Harper, et al., "Extraction of nuclear DNA from rhinoceros horn and characterization of DNA profiling systems for White (*Ceratotherium simum*) and Black (*Diceros bicornis*) rhinoceros", Forensic Science International: Genetics, vol. 7, 2013, pp. 428-433.
Hieronymus, et al., "Structure of White Rhinoceros (*Ceratotherium simum*) Horn Investigated by X-ray Computed Tomography and Histology With Implications for Growth and External Form", Journal of Morphology 267, Wiley-Liss, 2006, pp. 1172-1176.
McKittrick, et al., "Energy absorbent natural materials and bioinspired design strategies: A review", Materials Science and Engineering C, vol. 30, Elsevier, 2010, pp. 331-342.
PCT Invitation to Pay Additional Fees dated Jan. 12, 2016 for PCT application No. PCT/US15/51721, 2 pages.
Search Report and Written Opinion dated Mar. 3, 2016 for International Application No. PCT/US15/51721.
Sheng-Qing, et al., "Analysis of Rhinoceros Horn and Its Substitutes by IR Spectrometry", retrieved on Feb. 23, 2016 from <<http://www.rhinoresourcecenter.com/pdf_files/132/1324806757.pdf>>, Chinese Journal of Spectroscopy Laboratory, vol. 28, No. 6, Nov. 2011, pp. 3186-3189.
Tombolato, et al., "Microstructure, elastic properties and deformation mechanisms of horn keratin", Acta Biomaterialia 6, 2010, pp. 319-330.
Turner-Walker, et al., "Identification of animal hard tissues using Fourier transform infrared spectroscopy", retrieved on Feb. 23, 2016 at <<http://www.researchgate.net/publication/267640153>>, Natural History Collections, ICOM-CC, 17th Triennial Conference 2014 Melbourne, 2014, pp. 1-11.

* cited by examiner

*Primary Examiner* — Michael Barker
(74) *Attorney, Agent, or Firm* — Lee & Hayes PC; C. Rachal Winger; Katherine M. Mead

(57) ABSTRACT

Rhinoceros horn analogs and methods of synthesis thereof. Compounds with medicinal effects can be incorporated into the analogs. Genetic fingerprints can also be incorporated into the analogs. The analogs can be formulated into compositions.

17 Claims, 10 Drawing Sheets
Specification includes a Sequence Listing.

FIG. 5

| | 510 | 520 | 530 | 540 |
|---|---|---|---|---|
| | SEQ ID NO:1 | GATCAGTAACACCAAAATCCgtgtgtgtgtgtgtgtgtgtgtgt gcatgtgtgtaggcaggggggacattggtcacaactaacacatgaaggaat gagaaaatcccatgttgagttgaacagtaatagggtatacaacaatttctaat attgcatttggataatgctagtcttgatttcttttttgttgtatattttccattttttctcatat tatgtccttgGTGATCCTTCTGTCTTCACT | 16 | 17 (0.759) 18 (0.241) |
| | SEQ ID NO:2 | AGATTCTTGGAAAGGTCACTcaaggcacacagaaaatgcctc ctacacacacacacacacacacacacgcgcacacacacacatacacac gcacacacacctgacagcacatgttctcctGAGGTGAAACCCAAT GTT | 27 | 26 (0.727) 27 (0.273) |
| | SEQ ID NO:3 | ACATGTGTAAACTTGGGAACtgttgttagtcatgtttctccactca gaatgagaaacggagaaatccagaatgcagaaatagaaacgactgaag cagaaagacacaaaatgtgtgtgtgtgcatgtgtgtgtgtgtgtgtgtgtgt gtgtgtgagagagagagagaaagagggagagagagagggagaga gagattggaagtgggtgggattaagtaggGAGAAGAGATCAATG AACCA | 42.1 | 40 (1.000) |
| | SEQ ID NO:4 | TCATTTCTCTGTTCCCCATAGGACaaagtggggctcagaaa atatttgatctcacacacacacacacacacacacacacacacatttacatgcatt agtgctaacatcttatCCTTCACATATCGGTGGATATTGCT | | 14 (0.618) 15 (0.118) 18 (0.042) 24 (0.223) |
| | SEQ ID NO:5 | TAAGTCACAGGGACTAATCTGtaaaattgagataataatagga ccctgctcccaacacacacacacacacacacacacacacacacacttcagtg ggttgttatgaccaccagatgagacaatatatgtaaaatactttgcCTGATT CACAATAAACCCTC | 15 | 19 (0.847) 20 (0.153) |
| | SEQ ID NO:6 | ATCTTCCTCAGCAATAAGGggaggattagcaacggatgttagct cagggctaatcttcctcacacacacacaaaaattcattataaatttaactcttag agtaaaaactcttcattctccttcagtccctagaggaattgagaaatagtccca aactcagtggcagagaatcaagtttagaatatgaaaaatgtctagcaaaatt actcttttacacaGAACTGGAAACTCTGATGAT | 6.1 | 10 (1.000) |
| | SEQ ID NO:7 | AGGGTGGAATGTCAAGTAGcggggctgatattttccacgtttcca gtttctttaatttgcctgtggctgagctggcgctgggagccccacctccattctgt gtgtgcctgtgtgtgtgtgtgtgtgtgtgtgtgtgtgtgtgtgtgttggaaggtggc agaggcaggggtggggcaacaagctgggggcagggaCTCCTAGT CTCCCTCTAGAAG | 24 | 20 (0.255) 21 (0.018) 24 (0.727) |
| | SEQ ID NO:8 | CATGTGAAATGGACCGTCAGGcattggcaggaagcagcttgg aggtttccacgggacgcgtagctcctggcttggcaggtgtggtggcttgtgtatg tgatagcagcgcgcacacacacacgcgcgcacacacacacacacacaca cacgagccaggggcatcccccacttaccctgggctcttttggaaatatccat gccccCTGCCCCTTCCCAGAAAT | 22 | 20 (0.324) 21 (0.354) 22 (0.322) |

FIG. 5 CONT.

| 510 | 520 | 530 | 540 | |
|---|---|---|---|---|
| SEQ ID NO:9 | CCAGGTGAAGGGTCTTATATTTAGCaagctatctatattagg atatgtggagggaaattttctttttattgttttgacatatttggcatttttatccttttgcg ctatttttttttgtgtgtgtgtgtgtgtgtgtgtgtatgtgtgtgtgtgtgtgtgagga agatcagccctgaGGTAACATCCATGCCAATCC | 22 | 21.1<br>22<br>22.1<br>23 | (0.020)<br>(0.293)<br>(0.130)<br>(0.557) |
| SEQ ID NO:10 | CAGTGAGGAAGATTGGTTGCaataacttatggtaaataaattat caaatatttaaaaaattgcatggaactacacacacacacacacacacaca cacacacacaaatgcaggtcaaaCTGGTGACGTGTGAGTCA GG | | 22<br>23 | (0.298)<br>(0.702) |
| SEQ ID NO:11 | GAATGCTGATCATTTAGTGACaagtgaaaacacacacacac acacacacacacacacacacacacacacacacagcgatgttaaggaaa ggtctgtatgacttccaggaggacgttgggtgaaaagagaaggaagtgga atcttggactatgaaaaaatGTGATATCTCAACTGGACCC | | 18<br>21 | (0.373)<br>(0.627) |
| SEQ ID NO:12 | ATGGTGGAAGAAGTGCAGCCttgtgactggtgaccacaccag aaagatgcagtgggggaggagaggctctaaaaatggagaacaaaacaa taatggctcattgtaaagatgaagataggcattcagactaacagcatcacac acacacacacacacacacacacactgaatgcacagtatgtgctgagtaGGC GCTAGAGACACAGAAGT | | 16 | (1.000) |
| SEQ ID NO:13 | CTTGAGCAGAGTAGAATTTGGcatattcaagaaacagataga attccatcactgctggaatatattggagaaaggagtacctctctctctctttctct gtctctctcttacacacacacacacacatacacacacactccaatttccctgat acacacagcatacgaaataGGAATGAGGTGGATACAGAG | 14 | 16<br>17 | (0.566)<br>(0.434) |
| SEQ ID NO:14 | CAGCACAATGTTTGGCACTTGtaagtgctctgtaaatgtcaattc cctgccagcctaacacacacacacacacacacacacacacacacacaca cagacacctgcccccctatcgcagcctttgaattgcaggtgtaagtctttgtaaat atccttGGTGGTGACACAAGACTCCAA | 19 | 18 | (1.000) |
| SEQ ID NO:15 | CTGCCTTAACGACTGAACTGCctgattttgtgtgtgtgtgtgtgt gtgtatgtatgtgcgtatGTGGCATGAGATAACCTCCA | 16 | 21<br>25 | (0.732)<br>(0.268) |
| SEQ ID NO:16 | GTTTATACTATGCCCTGCACattttaaaaaaccctccacacaca gaaacacaacacacacacacacacacacacacagagagacatgctt atagcaagtaagcagttttgcagatctcacatttgggaatagtgaatgtcttaa gttccaaaatttatacCAATCTATTCAGTAGCATCC | 15.1 | 18<br>19<br>20 | (0.161)<br>(0.038)<br>(0.801) |

FIG. 5 CONT.

| | 510 | 520 | 530 | 540 |
|---|---|---|---|---|
| SEQ ID NO:17 | AGGTGATTAGGGAATTGCTGGgtcccaaccccagagtttttg attcagtaggtctgggtggggccaaaaaatctgaaagagtttcagttgctg ggaacaggaggggtgtgtatgtgtgtgtgtatgtgtgtgtgtgtgtgtgt gtgtgtgtgttagggagatcggagtaggaggataagggaagatgcttct ttagatttgaatgttaagaaacGCAATGCCAGGACAGAAGAA | 26 | 14 (0.346)<br>20 (0.382)<br>24 (0.272) |
| SEQ ID NO:18 | AACCAACTTGTAATGAGAGGgctaccaaacctttctgtgtgtg tgtgtgtgtgtgtgtgtgtgagtgtgtgtgtgggcctttttccaccattccaat attttttcccctcgtttcccttctttctctctttatgcgaatgtaagagaatgtggc ttaacttcaactctagtgactgttctttcccgcaagtgtgtgtgtgcgcGTC TTCCTTCCTGTTCATT | 20 | 19 (0.090)<br>21 (0.655)<br>22 (0.255) |
| SEQ ID NO:19 | TTCAGTTCAGTTTTTGCTCtgagtattatgttgcttggaagaag gaataggattctccctctctctctctctctctctctctctatatatatatatatat atatataaagattcaaagtaagaatctttGTAGAAGAAGCATGG ATGGATGAG | 24 | 21 (0.083)<br>24 (0.258)<br>25 (0.660) |
| SEQ ID NO:20 | ACAGCTAGAATCACCAAAACaagaaggcttatgagaaaa attagggttaggagtcaccactcaaaaccttcagaagtttgtaatatatgt ctgtatatacatatatactcaggtgttttatatatttatatatatatatatataca cactaagatattttatacacatataatataataatacacacacacacaca tacacacacacacacacacactGAGATTTATGCAGCAGGA | 16 | 12 (0.513)<br>19 (0.487) |
| SEQ ID NO:21 | CTAGCAAAATACTCAAAGAGGtttgatccaaccattcaaatt gtttagtatataccctggtggttgagcactgctagaacacacacacaccc ccatacgcaaacacacacacacacacacacacacacacacacaga ttgctgccaccaaataaatgagtggtctccaactatccctgggccCTT GGTGATTCCCTTAGTAA | 22 | 21 (0.506)<br>22 (0.447)<br>23 (0.048) |
| SEQ ID NO:22 | GGCAAAACTAAGAGAACTTGtgaaaaacacacacacac acacacacaccaaaagaaaaaacaaaagcatcttgcctattaattg aagttcttaaagaggaaaaaatagtgccctctcactgactctcaagcc aatcctatgagttcgggtttCCATTTCCAGTTTCCTATC | 11 | 18 (0.416)<br>20 (0.123)<br>24 (0.003)<br>25 (0.458) |
| SEQ ID NO:23 | GATTTGGAAGCTAGGCATTTCCtacggtcttgctatagtaa atgtcataaaacccattacctagaatggggaatttcTGTCATTCAT GAGTATCATGGC | N/A | N/A |
| SEQ ID NO:24 | GATTTGGAACCTAGGCATTTCCtatagtcttgtatataaata tagtgtatgcccataaagcccattagctagatagggaatttcTGTCAT TCATGAGTATCATGGC | N/A | N/A |

FIG. 6

| 610 | 620 |
|---|---|
| SEQ ID NO:25 | MTGSCCGSSFSSRSLGGGCCQPCFSRDPCCGRPVFYRTTVCRPVTCVPRYTRTICEPSRRPLC CDPCSLQEGCCRPITCCPTSCTAVVCRPRCWASTCCRPISVQSPCYRPSCCQPAPCHTICRTS HC |
| SEQ ID NO:26 | MSYNFSTRNCSSRPIGGRCTVPVAEVAIPSTQADCLSGISLPSSFQTGSWLLNHCQETCCEPTV CQPTCYQQTSCVSRPGQVTCSRQTTCVSNPCSTTCSRPLTFISRGCQPQVSISTVCQPVGGIST VCQPACGVSRTYQQSCVSSCRRIC |
| SEQ ID NO:27 | MSYNCCSGKFSSCSLGGYLRYPRSSCGSSYPSKLIYRTDLCSPSTCQLGSSLYRNCQRTCWEP TRYQTPCVVSRPCQTSSYGLRTSTLRSPCWTTYAGSLGFGSRSCYSLGCGSSVFKPLGYRVCG FPALGYGSRFCCPTYFPSRSCQFSCYRPTFRSAFCRSTC |
| SEQ ID NO:28 | MEMNGDKVDHSKKASIQMDIEPLIHSSFHCNSAELTTPVNMSYSCCSGNFFSCSLGGYLHYPGS SCGSFYPSNLVYHTDLWSPSPCQRSCYRPRTSIRCISCWPTYAASLGSGSSSCCSLSYGSRSC YSLGCGSRGFRPLRYGVCGFPCLSYGSRFCRPIYFASRSCQSSCYRPACRSIFYQSTC |
| SEQ ID NO:29 | MISTCSPASIKNCPRPSSVCSSSMSCRPELCLGYVCQPVTCMPSICTPTTYRPASCLSKTYLSSS CRPASGISSSLGTCSWYCEGTFNGSEKETMQFLNDRLASYLEKVRQLERENAELEGKIQEACQA QVPICPDYQSYFRTIEELQQKVLCTKAENARMVVHIDNAKLAADDFRTKYETELAMRQLVEADTN GQRRILDELTLCKADLEAQVESLKEELLCLKKDHEEEVSALRCQLGDCLNIEVDALPPVDLNRML EEMRCQYEAVVETNHRDVEEWFNTQMEELNQQVATSSEQLQSYQSDIDLRRTVNTLEIELQAQ HSLRDSLENTLTETEARYSSQLAQMQGLITSVEAQLAEIRCDLERQNQEYRVLLDVKARLEGEIN TYWGLLESEDCKYVGPAEAVQRHVCEGWGRP |
| SEQ ID NO:30 | MATTIRQFTSSSSIKGSSSGLGGGSSRMSCRVSGGGLGAGSCRLGSTSGLGSALGGSSYSSCYSF GSGGGYGGGYGGGYGGGYGSSFGGVEGLLAGSEKATMQNLNDRLASYLDKVRALEEANAEL EVKIRDWYQKQAPGPAPNYSHYFQTIEDLKNKILAATVDNASILLQIDNARLAADDFRTKFETEQA LRLSVEADINGLRRVLDELTLARADLEMQIENLKEELAYMRKNHEEEMNALRGQVGGEINVEMD AAPGVDLSRILNEMRDQYEKIAEKNRKDAEDWFFSKTEELNREVATNSELVQSGKSEISELRRTL QALEIELQSQLSMKASLEGSLAETENRYCMQLSQIQGLISSVEEQLAQLRCEMEQQNQEYKILLD VKTRLEQEIATYRRLLEGEDAHLTQYKPREPVTTRQVRTIVEEVQDGRVISSREQVHQTTH |
| SEQ ID NO:31 | MATQICSPIFSSGSVRGLCGTAGGITRVSSVRSVGGLPCQRLGSTPSLAGAARSASSIRLGLSGFGTCLPA SCLSTGCYPSSFVGGSWFCEGTFNGNEKETMQFLNDRLANYLEKVRQLEQENAELESRIREW YESQIPYICPDYQSYFRTIEELQQKILLTKAENARLVLQIDNAKLAADDFRTKYETELGLRQLVEAD TNGLRRILDELTLCKADLEMQVESLKEELLCLKKNHEEEVNVLRGQLGDRLNVEVDAAPSVDLNK ILDDMRCQYETLVENNRRDVETWFNTQTEELNQQVVSSSEQLQSCQVEIIELRRTVNALEIELQA QQSTRNSLESTLAETEARYSSQLAQMQGLITNVEAQLAEIRCDLERQNHEYQVLLDVKARLESEI ATYRRLLESEDCKLPAHPCATECKPAIRVPYVSTVPCAQASQVSAQIRTITEEIRDGKIISSREHLQ PCPL |
| SEQ ID NO:32 | MTTCSRQFTSSSSLKGSYGIGGGSSRISSILGGGSYQAPSAYGGGLSVSTRYSSGGACGLGGG YGGGFSSSSSFGGALGSGFGGGYGGGLGAGFGAGFGGGFIGGDGGLISGNEKITMQNLNDRL ASYLDKVRALEEANAELEVKIRDWYLKQRPTEPKDYSPYFRTIEDLRNKIITATIENAQPILQIDNA RLAADDFRTKYEHELALRQSVEADINGLRRVLDELTLARTDLEMQIESLKEELAYLRKNHQDEMN ALRGQTGGDVNVEMDAAPSVDLSRILNEMRDQYEQIAEKNRRDAEAWFLRKTEELNKEVASNS ELVQTSRSEVTELRRVLQGLEIELQSQLSLKASLENSLEETKGRYCMQLAQIQGLISSVEEQLAQL RCEMEQQSQEYQILLDVKTRLEQEIATYRRLLEGEDAHLSSQHTSSQSYSSRDVISSSSSTSSSR QTRSILKEGSSSFSQGQNSKP |
| SEQ ID NO:33 | MTTCSRQFTSSSSLKGSCGIGGGSSRISSVLGGGSYRAPSAYGGGLSVSTRYSSGGACGLGGG YGGGFSSSSSFGGALGSSYGGGYGGGLGAGLGGGFGGGIGGGFGGGFGGGDGLLVGSEKVT MQNLNDRLASYLDKVRALEEANADLEVKIRDWYQKQRPAEIKDYSPYFKTIEDLRNKILTATVDN ANVVLQIDNARLAADDFRTKYETELNLRLSVEADINGLRRVLDELTLARTDLEMQIESLKEELAYL RKNHEEEMNSLRGQVGGDVNVEMDAAPGVDLSRILNEMRDQYEKIAEKNRKDAEDWFFSKTE ELNREVATNSELVQSGKSEISELRRTVQNLEIELQSQLSMKASLENSLEETKGRYCMQLAQIQELI SSVEEQLAQLRCEMEQQNQEYKILLDVKTRLEQEIATYRRLLEGEDAHLSSSQFSSGSQSSRDV TSSSRQIRTKIMDVHDGKVVSTHEQVLRTKN |
| SEQ ID NO:34 | MTCGSYCAGRAFSCASACGPRPGRCCITAAPYRGVSCYRGLSGGFGSRSLCGGFRAGSCGRS FGYRSGGVRGPSAPCITTVSVNESLLAPLNLEIDPNAQYVKQEEKEQIKSLNNRFAAFIDKVRFLE QQNKLLETKLQFYQNRKCCESNLEPLFSGYLETLRREAERVEADSGRLASELNHVQEVLEGYKK RYEEEVSLRATAENEFVALKKDVDCAYLQKSDLEANAEALTQEVDFLRRLYEEEIRVLQAHISDT SVIVKMDNSRDLNLDSIVAEIKAHYDDIASRSRAEAESWYRTKCEEIKATVVRHGETLRRTKEEIN ELNRLIQRLTAEIENAKCQNSKLEAAVAEAEQQGEAALSDARSKLAGLEGALQKAKQDMACLLR EYQEVLNSKLGLDIEIATYRRLLEGEEQRLCEGVGSVNVCVSSSRGGIVCGDLCASGAAPAVTTS VCSAPCSGNVVVGTANACAPCTLGCKRCHHHHHH |

FIG. 6 CONT.

| 610 | 620 |
|---|---|
| SEQ ID NO:35 | MTCGFSSVGCGFSPRTFSCASACGPRPGRCCITAAPYRGVSCYRGLSGGFGSRSLCGGFRAG SCGRSFGYRSGGICGPSAPCITTVSVNESLLAPLNLEIDPNAQCVKHEEKEQIKSLNNRFTAFIDK VRFLEQQNKLLETKLQFYQNRKCCDSNLELLFSGYLETLRREAECVEADSGRLASELNHVQEVL EGYKKRYEEEVTLRTTAENEFVALKKDMDCAYLRKSDLEANAEALTQEVDFLRRLYEEEIHVLQA NISDTSVIVKMDNSRDLNLDSIVAEIKAQYDDMASRSQAEAESWYCTKCEEIKATVVRHGETLRR TKEEINELNRLIQRLTAEIENAKCQNSKLEAAVAEAEQQGEAALSDARSKLAGLEGALQMAKQDM ACLLREYQEVLNSKLGLDIEIATYRRLLEGEEQRLCEGVGAVNVCVSSSQGGIICGDLCVSGSRP VAGSVCSAPCGGNLVVSTGLCAPCSQLNTTTGSCGLGRC |
| SEQ ID NO:36 | MDTKGYITTISSSTPCQSCSRITNFRTISSNTNCQHGGLKANSCQPTGHVLKTRQTPGCQHTPCL CLTPICLISNFNACPSADDCGWGGEGINSNEKETMQVLNDRLANYLEKVRMLEQENAELECKIQ EESNKELPVISPDYLSYYATIEELQQKILCTKAENSRLVSQIDNTKLAADDLRAKYEAEVSLRKQV EADANGVQHILNALTLGKADLEAQVHSLKEELICLKNNHEEEINSLQSQLGDRLNIEVTTAPSVDL NRVLQEMRCQYESIMETNSRDVEQWFNTQTEELNQQVVTGSQQQQCCQKEIIELRRTMNILEV ELQAQHRMRDSQECILAETEARYAALLAQIQRLIDNLEAQLAEIRCALERQNQEYEILLDVKSRLE CEITTYRSLLESLDGKFACNPCAIKCEPSTCTFSKARAKECTSPIYMSSAPREICEPCSACGALSR ILVKICTITKEIKDGKVISSHEHVQPCFITRPAKV |
| SEQ ID NO:37 | MSCRSYRISSGCGVTRTFSSCSAVAPRTGSRCCISAAPYRGVSCYRGLTGFGSRSLSNLGSCG PRLAVGSFRAGSCGRSFGYRSGGVCGPSAPCITTVSVNESLLAPLNLEIDPNAQCVKQEEKEQI KSLNNRFAAFIDKVRFLEQQNKLLETKWQFYQNQRCCESNLEPLFSGYIETLRREAECVEADSG RLASELNHVQEVLEGYKKRYEEEVALRATAENEFVVLKKDVDCAYLRKSDLEANVEALVEESSFL KRLYDEEIRVLQAHISDTSVIVKMDNSRDLNLDSIVAEIKAQYDDIASRSRAEAESWYRTKCEEIKA TVVRHGETLRRTKEEINELNRLIQRLTAEIENAKCQNSKLEAAVAEAEQQGEAALNDARCKLAGL EEALQKAKQDMACLLREYQEVLNSKLGLDIEIATYRRLLEGEEQRLCEGVGVSNVCVSSSRGGG ISCGGLTYSTTPGRQIASGPSAIGGSITVMAPDACAPCQPRPSSFSCGSSRSVRFA |
| SEQ ID NO:38 | MSRQSSVSFRTGGSRSFSTASAVTPSVSRTSFTTVSRSGGGGGGFGRVSLGGACGVGGYGSR SLYNLGGGFGFGGGAGSGFGFGGGAGGGFGLGGGAGFGGGFGGPGFPVCPPGGIQEVTVNQ SLLTPLNLQIDPAIQRVRTEEREQIKTLNNKFASFIDKVRFLEQQNKVLDTKWTLLQEQGTKTVRQ NLEPLFEQYINNLRRQLDGILGERGRLDSELRNMQDLVEDFKNKYEDEINKRTTAENEFVMLKKD VDAAYMNKVELEAKVDALMDEINFMRMFFEAELSQMQTHVSDTSVILSMDNNRSLDLDSIIAEVK AQYEEIANRSRTEAESWYQTKYEELQQTAGRHGDDLRNTKHEISEMNRRMIQRLRAEIDNVKKQC ANLQAAIADAEQRGELALKDARNKLAELEDALQKAKQDMARLLREYQELMNTKLALDVEIATYRK LLEGEECRLSGEGVGPVNISVVTNTVSSAYGGGSGFGGSLGGGLGGGLGGGLGGGSGGGYYS SSSGGVGLGSGLSVGGSGFSAGSGLGLGVGLGGGGGSSSSVKFVSTTSSSRKSFKS |
| SEQ ID NO:39 | MPLKHYLLLLVGFQAWGAGLAYYGCPSECTCSRASQVECTGARIVAVPTPLPWNAMSLQILNTH ITELSESPFLNISALIALRIEKNELSHIMPGAFRNLGSLRYLSLANNKLQVLPIGLFQGLDNLESLLLS SNQLVQIQPAHFSQFSNLKELQLHGNHLEYIPDGVFDHLVGLTKLNLGKNSLTHLSPRVFQHLGN LQVLRLYENRLSDIPMGTFDGLGNLQELALQQNQIGMLSPGLFHNNRNLQKLYLSNNHISQLPLG IFTQLPQLNRLTLFGNSLKELSPGIFGPMYNLRELWLYDNHITSLPDNVFSSLHQLQVLVLSRNQI SFISPGAFNGLTELRELSLHTNALQELDGHVFRMLANLQNISLQNNRLRQLPGNIFANVNGLMTIQ LQNNQLENLPMGIFDHLGNLCELQLYDNPWRCDSDILPLHNWLLLNKPRLRIDTLPVCFSPANVR GQSLIIININAAFPSVQVPEITDVPSKPETPRYPDTSSYPDTTSISSTTEFISPVDYTDLNTIVTTNAH STLGMTQAQSGLAJAAIVIGIIALACSLAACICCCCCKKKSHAVLMQMKAPNEC |
| SEQ ID NO:40 | MSCRSYRVSSGHRVGNFSSCSAGIPRNLNRFRASSVSCRSGPSFRGIGGFGSRSVITFGSCSP RIAAVGPRPIRCGVGFGAGSGMAFGFGDGIGAGLGFGAGSCLGYGFGGPGFGYRVGGIGVPAA SSITPVTVNQSLLTPLNLEIDPNAQRVKRDEKEQIKTLNNKFASFIDKVRFLEQQNKLLETKWSFL QEQKGARSNLEPLFENYITNLQRQLDIANSERARLEAERNQLQDVLEGFKKKYEEEVVFRANAE NEFVALKKDVDAAFLNKAELEANVDTLTQEIDFLKTLYAAEIQLLQSHISETSVIVKMDNSRDLDLD GIIAEVRAQYEEVAKRSRADAEAWYQTKYEEMRVTAGQHCDNLRNTREEINELTRLIQRLKAEIE HAKAQRARLEAAVAEAEQQGEAALNDAKCKLADLEAALQQAKQDMARQLREYQELMNAKLGL DIEIATYRRLLEGEEIRICEGVGPVNISVSSSRGGVVCGPESLVTSSTLSRSGVTFSGSSSIRPSG ACGSSLGGVVVAGGDPLCAGSRGGSVLVGEACIPSVPCPLPTEGFSSCSGGRSSSLRFVSTTT RRTKY |

FIG. 6 CONT.

| | |
|---|---|
| SEQ ID NO:41 | MSRQSSVSFRTGGSRSFSTASAVTPSVSRTSFTTVSRSGGGGGGFGRVSLGGACGVGGYGSR SLYNLGGSKRISISASGGGFRNRFGAGAGGGFGFGGGAGSGFGFGGGAGGGFGLGGGAGFG GGFGGPGFPVCPPGGIQEVTVNQSLLTPLNLQIDPAIQRVRTEEREQIKTLNNKFASFIDKVRFLE QQNKVLDTKWTLLQEQGTKTVRQNLEPLFEQYINNLRRQLDGILGERGRLDSELRNMQDLVEDF KNKYEDEINKRTTAENEFVMLKKDVDAAYMNKVELEAKVDALMDEINFMRMFFEAELSQMQTHV SDTSVILSMDNNRSLDLDSIIAEVKAQYEEIANRSRTEAESWYQTKYEELQQTAGRHGDDLRNTK HEISEMNRMIQRLRAEIDNVKKQCANLQAAIADAEQRGELALKDARNKLAELEDALQKAKQDMA RLLREYQELMNTKLALDVEIATYRKLLEGEECRLSGEGVGPVNISVVTNTVSSAYGGGSGFGGS LGGGLGGGLGGGLGGGSGGGYYSSSSGGVGLGSGLSVGGSGFSAGSGLGLGVGLGGGGGS SSSVKFVSTTSSSRKSFKS |
| SEQ ID NO:42 | MSRCFSSVSGRRGGAGFSSGSAGVVSFQRRSTSSSVRRSGGGGGGFSRGRCGAGGAGGGF GSRSLVNLGGSKSISISVAGGGRRSGFGGGYGGSSFGGGGYGGGGFGGGFGSGGFGGGFGS GGFGGGIGIGGGFGGGGFGGGFGPVCPPGGIQEVTINQSLLQPLNVEIDPEIQRVKSREREQIKT LNNQFATFIDKVRFLEQQNQVLQTKWELLQQVDTSTRTYNLEPLFESYINTLRRQVEQLKNDQP RLDSELKNVQDLVEDYRRKYEEEINRRTNAENEFVTIKKDVDAAYLTKVDLQAKVDNLRQEIEFLT ILYQEELSQLQTHISDTNVILSMDNNRFLDLDSIIAEVKAQYEEIAQRSKAEAEALYQTKYEELQITA GKHGDSLRDSKIEISELNRVIQRLRSEIDSVKKQISALQQSISDAEQRGENALKDARNKLAELEDA LQKAKEDLARLLRDYQELMSTKLALDLEIATYRTLLEGEEVRMSGECAPNVSVSVSTSHTSISGG GIRGGGAFSSGGGGGYSSGGGYSSGGGGGGYSSGGISGSQRGVSGGGGGSTGGWASGGG GSGGSFSSSGGRVISSGGSKTSGGSSSVKFVSSSYSRGTR |
| SEQ ID NO:43 | MPYNCCLPNVSCCSSFSSRPCVPPSCRSCTLPGACNIPANVGSCSWFCEGSFNSNEKETMQFL NDRLASYLEKVRQLERDNAELESRIRERSQQLEPGVCANYQSYFRTIEELQQKILSAKSENARLV LQIDNAKLASDDFRTNTMPYNCCLPNLSCRSTFSARPCVPPSCRSCTLPGACNIPANVGSCSWF CEGSFNGSEKETMQFLNDRLASYLEKVRQLERENAELESRIRERSQQQEPEVCANYQSYFRTIE ALQQKILSSKAENARLVVQIDNAKLAADDFRTKYETELGLRQLVESDINGLRRILDELTLCRSDLE AQVESLREELISLKQNHEQEVNSLRSQLGDRLNIEVDAAPTVDLNRVLNETRSQYEALVETNRRD VEEWFTTQVGISARGRSGPELSQVQGLITSVESQLAEIRSDLERQNQEYQVLLDVRARLESEINT YRGLLESEDCNTMSYNCCLPNLSCRSSFSARPCMPPSCRSCTLPGACNIPANVGSCSWFCEGS FNSSEKETMQFLNDRLASYLEKVRQLERDNAELESRIRERSQQQEPEVCANYQSYFRTIEALQQ KILCTKSENARLVVQIDNAKLAADDFRTKYETELGLRQLVESDINGLRRILDELTLCKADLEAQVES LKEELLCLKQNHEQEVNTLRSQLGDRLNVEVDAAPTVDLNSVLNATRSQYEALVETNRRDVEE WFTTQTEELNRQVVSSSEQLQSYQAEIIELRRTVNALEVELQAQHNLRDSLENTLTETEARYSAQ LSQVQGLITSVESQLAEIRSDLERQNQEYQVLLDVRARLESEINTYRGLLESEDCKLPCNPCATT NACDKSIGSCISNPCAPRTRCGPCNTFVC |

SYNTHETIC RHINOCEROS HORN ANALOGUES

CROSS REFERENCE TO RELATED APPLICATION

This applications is a U.S. National Phase application based on International Patent Application No. PCT/US2015/051721, filed on Sep. 23, 2015, which claims priority to U.S. Provisional Patent Application No. 62/053,990 filed Sep. 23, 2014, the entire contents each of which are incorporated by reference herein.

FIELD OF THE DISCLOSURE

The present disclosure provides synthetic rhinoceros horn analogues and methods of synthesis thereof. Compounds with medicinal effects can be incorporated into the analogues. Genetic fingerprints can also be incorporated into the analogues. The analogues can be formulated into compositions.

BACKGROUND OF THE DISCLOSURE

There are five extant species of rhinoceros, three in Asia and two in Africa. Due to successive waves of poaching and habitat destruction, the majority of the remaining rhinoceroses belong to one of the two African species: *Ceratotherium simum* (white) or *Diceros bicornis* (black). Now, even those species are threatened. The threat comes from a renewed demand for rhinoceros horn in East and Southeast Asia. While rhinoceros horn has been prized by many cultures for a variety of reasons, its current resurgence is due, in part, to its past use in Traditional Asian Medicine (TAM). A full explanation of TAM and its transmogrifications is beyond the scope of this disclosure; however, in Western terms, the putative medicinal indications of rhinoceros horn include alleviating fever, reducing pain, fighting infection, preventing or eliminating hangover, curing cancer, and increasing sexual function.

New technologies to ameliorate the rhinoceros poaching crisis are being developed. Unfortunately, many of these technologies have inherent disadvantages. For instance, autonomous drones, which can be used to patrol rhinoceros ranges, may be appropriated by poachers to hunt rhinoceroses. This might occur through computer hacking of legitimate drones, corruption of legitimate drone operators (so-called "khaki collar crime"), or deployment of illegitimate drones. Another technology with an inherent disadvantage is the genetic fingerprinting of rhinoceroses. It is true that DNA profiling systems can help law enforcement solve wildlife crimes. At the same time, though, such systems can also be used by consumers to identify counterfeit horn (e.g., water buffalo horn), thereby putting more pressure on the black market to deliver authentic rhinoceros horn. Finally, an apparatus to automatically scrape horn from a domesticated rhinoceros is disclosed in the literature (Chinese Patent CN 100407907 C). Ethical concerns aside, the farming of rhinoceroses for their horn cannot scale to meet growing demand. That is, harvesting is constrained by the number of rhinoceroses in existence, birth rates, death rates, and the rate of horn growth per animal.

SUMMARY OF THE DISCLOSURE

The present disclosure provides synthetically created rhinoceros horn analogues. The disclosed analogues and methods have several advantages. For one, the disclosed analogues are practically indistinguishable from authentic horn, making them acceptable substitutes for the real thing. Furthermore, the disclosed analogues may be purer (e.g., contain less pollutants) than rhinoceros horn. In certain situations, they may be more efficacious, potentially making them preferable to natural rhinoceros horn. A particular advantage of the disclosed methods is that they scale. That is, they make it relatively easy to adjust production in response to changes in demand. The disclosed methods are also less resource intensive in terms of time, security, land, and provisions. Another advantage is that neither the disclosed analogues, nor their attendant methods, are dual-use, meaning they cannot be misused to facilitate crimes against wildlife.

BRIEF DESCRIPTION OF THE FIGURES

FIG. 5 is a table giving the SEQ ID NO, DNA sequence (written 5' to 3' end with primer regions capitalized), putative allele (in dinucleotide repeats) within the DNA sequence, and previously observed alleles for each locus of a known DNA profiling system.

FIG. 6 is a table that lists the amino acid sequences of the hard keratins present in the white rhinoceros.

DETAILED DESCRIPTION

Figure 1:
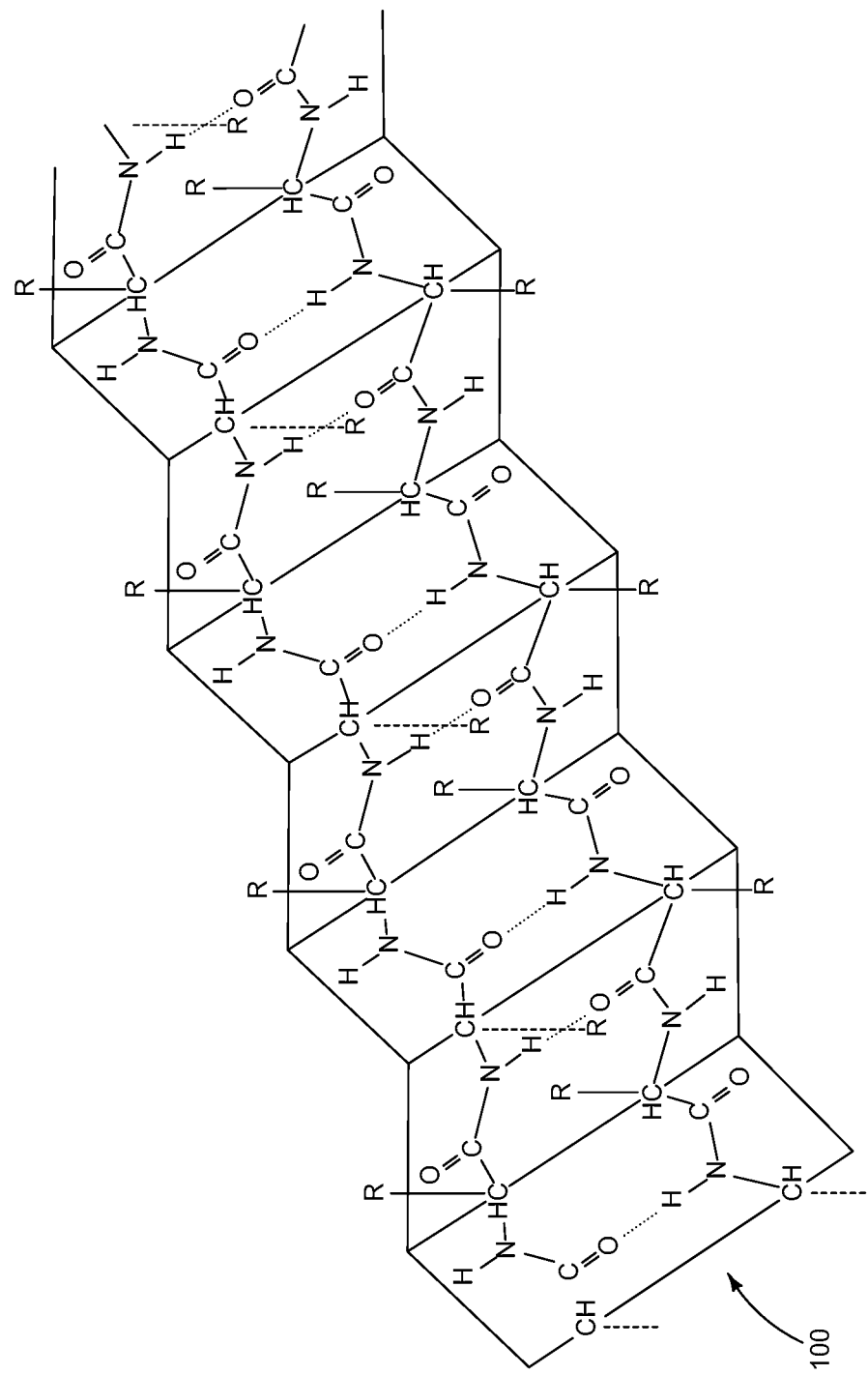
FIG. 1 depicts a chemical diagram of a β-sheet.

There are five extant species of rhinoceros, three in Asia and two in Africa. Due to successive waves of poaching and habitat destruction, the majority of the remaining rhinoceroses belong to one of the two African species: *Ceratotherium simum* (white) or *Diceros bicornis* (black). Now, even those species are threatened.

New technologies to ameliorate the rhinoceros poaching crisis are being developed. Unfortunately, many of these technologies have inherent disadvantages. For instance, autonomous drones, which can be used to patrol rhinoceros ranges, may be appropriated by poachers to hunt rhinoceroses. Another technology with an inherent disadvantage is the genetic fingerprinting of rhinoceroses. It is true that DNA profiling systems can help law enforcement solve wildlife crimes. At the same time, though, such systems can also be used by consumers to identify counterfeit horn (e.g., water buffalo horn), thereby putting more pressure on the black market to deliver authentic rhinoceros horn. Finally, an apparatus to automatically scrape horn from a domesticated rhinoceros is disclosed in the literature (Chinese Patent CN 100407907 C). Ethical concerns aside, the farming of rhinoceroses for their horn cannot scale to meet growing demand.

The present disclosure provides synthetically created rhinoceros horn analogues. The disclosed analogues and methods have several advantages. For one, the disclosed analogues are practically indistinguishable from authentic horn, making them acceptable substitutes for the real thing. Furthermore, the disclosed analogues may be more efficacious, potentially making them preferable to rhinoceros horn in certain situations. A particular advantage of the disclosed methods is that they scale. That is, they make it relatively easy to adjust production in response to changes in demand. The disclosed methods are also less resource intensive in terms of time, security, land, and provisions. Another advantage is that neither the disclosed analogues, nor their attendant methods, are dual-use, meaning they cannot be misused to facilitate crimes against wildlife. If necessary, a DNA watermark may be incorporated into the disclosed analogues in order to allay concerns of those who disagree with the aforementioned statement.

Rhinoceros horn mainly includes calcium and melanin in a keratin matrix. It is produced by epidermal cells that undergo keratinization and die in a manner similar to the growth of human hair and nails. These facts about rhinoceros horn belie the complexity of synthesizing substances analogous to it. The complexity is inherent in the creation of any physically hard biological substance that is created in vitro due to a lack of scientific advances in the secretion of proteins that require a highly reducing environment.

Embodiments of rhinoceros horn analogues include a keratin base in either a fibrous or small-sheeted structure, proteins and amino acids found in authentic rhinoceros horn, and a resultant substance with similar physical properties (e.g., hardness, density, color, brittleness, tensile strength, and optical representation) to that of authentic rhinoceros horn. In some embodiments, the keratin base may include α-helices.

As one example, the native composition of northern white rhinoceros horn includes 2% arginine; 5% lysine; 9% cholesterol; 3% taurine; 0.2%-1% hexosamines (fructosamine & glucosamine); and 0.2% sphingosine within the calcium and melanin containing keratin matrix. The variance of the above percentages can be as much as ±20% based on the diet of a wild rhinoceros. Accordingly, in particular embodiments, and particularly applicable to northern white rhinoceros, authentic rhinoceros horn can include: 1.6%-2.4% arginine; 4-6% lysine; 7.2-10.8% cholesterol; 2.75-3.25% taurine; 0%-1.25% hexosamines (fructosamine & glucosamine); and 0.1%-0.3% sphingosine.

Rhinoceros horn can also include a total inorganic content of: 66-70% sulfur, 15-19% potassium, 5-9% calcium, 0-3% iron, 0.2-0.4% titanium; and 0-4% zinc. Accordingly, inorganic content can include 66-70% sulfur; 15-19% potassium; 5-9% calcium; 0-3% iron; 0.2-0.4% titanium; and 0-4% zinc.

The physical properties of a rhinoceros horn can include a Shore A hardness of 92-96, a Shore D hardness of 68-72, and a Density of 1.122-2.222 g/cubic cm.

Analogues as described herein include synthetically created substances that physically resemble natural rhinoceros horns. Physically resemble means that the synthetically created substances match measured characteristics of natural rhinoceros horn. Matches need not be identical, but must be within measurement error or accepted variation, as understood by one of ordinary skill in the art for the particular characteristic and measurement technique utilized. Characteristics that can be measured include the physical characteristics of the analogue (e.g., hardness, density, surface morphology, color, texture, rate of decay, brittleness, tensile strength, and optical representation) and the chemical characteristics of the analogue (e.g., presence and percentage of organic components, presence and percentage of inorganic components).

In particular embodiments, for any given characteristic measurement, the measurements resulting from a synthetic analogue and natural rhinoceros horn will not differ by more than 1%, more than 5%, more than 10%, more than 15% or more than 20%.

In particular embodiments, analogues will match at least one, two, three, four or five physical characteristics of a natural rhinoceros horn and at least one, two, three, four or five chemical characteristics a natural rhinoceros horn. For example, in particular embodiments, the analogues will match hardness and density characteristics and will match amino acid presence and percentage characteristics. In particular embodiments, the analogues will match hardness and density characteristics and will match inorganic component presence and percentage characteristics. In particular embodiments, the analogues will match hardness and density characteristics and will match amino acid presence and percentage characteristics and inorganic component presence and percentage characteristics.

While particular analogues resemble a natural rhinoceros horn upon visual inspection or particular physical characteristics, other analogues can be provided in powder form. Analogues provided in powder form will generally be assessed by measuring the presence and percentage of organic and inorganic components, rather than physical characteristics such as hardness and density. In particular embodiments, however, physical characteristics such as color of a powder can be included as a measurement. A powder includes particles of an analogue described herein: (i) produced by the grinding, crushing, or disintegration of a solid analogue; and/or (ii) before formation of a solid analogue form.

Various characteristics can be measured using analytical methods such as physical property testing, Fourier Transform Infrared (FTIR) spectroscopy, X-Ray Fluorescence (XRF), Short Tandem Repeat (STR) genotyping, and physical properties analysis.

In some embodiments, additional additives may be included in the rhinoceros horn analogue in order to recreate the medicinal effects that rhinoceros horn is believed to produce when consumed. The presence of such additives does not destroy a previous "match" as described above for an analogue. Such additional additives include caffeine, aspirin, acetaminophen, ibuprofen, sildenafil, tadalafil, combinations thereof, or the like.

In some embodiments, additional additives may be included in the rhinoceros horn analogue in order to mimic other characteristics of authentic horn. Such additional additives include tryptophan, histidine, aspartic acid, threonine, serine, glutamic acid, proline, glycine, alanine, cystine, valine, methionine, isoleucine, leucine, tyrosine, phenylalanine, carboxymethyl cysteine, ethanolamine, thiolactic acid, melanin, fibrous keratin, genetic material (DNA or RNA), trace elements, isotopes of trace elements, rhinoceros cells, combinations thereof, or the like.

The specific additives employed in making an analogue, as well as their relative percentages, may vary from embodiment to embodiment, and generally require experimentation for optimization. Nothing herein is intended to limit the point at which an additive is included in an analogue.

In embodiments including genetic material, it is recommended that a set of forensic loci known in rhinoceroses be amplifiable. One such set is described in the literature (Harper et al. "Extraction of Nuclear DNA from Rhinoceros Horn and Characterization of DNA Profiling Systems for White (*Ceratotherium Simum*) and Black (*Diceros Bicornis*) Rhinoceros," *Forensic Sci. Int.-Gen.* 2013; 7:428-433). It includes 22 STR loci and 2 gender loci. Ostensibly, this set is used to produce the DNA profiles found in the University of Pretoria's Rhino DNA Index System (RhODIS). Certain aspects of this set are shown in detail in FIG. 5.

Looking at column 510 of the FIG. 5, there is shown SEQ ID NO:1-22, designating exemplary DNA sequences for the 22 STR loci of the aforementioned set. SEQ ID NO:23 and SEQ ID NO:24 designate exemplary DNA sequences for the gender loci. The exemplary DNA sequences themselves are contained in column 520. SEQ ID NO:1-23 are from the May 2012 assembly of the white rhinoceros genome produced by the Broad Institute (CerSimSim1.0). SEQ ID NO:24 is from GenBank (accession number DQ520645). Column 530 contains allele calls for the exemplary DNA sequences in column 520, where applicable. The last column 540 contains the alleles observed in a sample of 367 white rhinoceroses and their corresponding frequencies in parentheses.

Referring now to SEQ ID NO:6 of FIG. 5, for example, it is seen that the exemplary DNA sequence has an allele call of 6.1 in column 530. This means that the sequence presumably has 6 dinucleotide repeats (12 bp) plus 1 incomplete repeat (1 bp) relative to a GenBank reference sequence. Here, the motif contains CA repeats and is underlined for clarity. In contrast, the only allele observed at-large in white rhinoceroses is 10 as found in column 540. If a sequence has an allele in column 530 but does not have a matching value in column 540, the discrepancy may be due to natural variation or the effects of different allele calling methods. Regardless, the information presented in FIG. 5 should be sufficient for those skilled in the art to forge DNA profiles.

In one embodiment including genetic material, SEQ ID NO:1-24 are made by phosphoramidite solid-phase synthesis along with their associated primers. Next, these synthesized sequences are amplified by Polymerase Chain Reaction (PCR). The PCR products are then diluted down for inclusion in the final rhinoceros horn analogue. A DNA profile of the analogue would be homozygous at all STR loci and would characterize it as male due to the presence of both gender loci (i.e., SEQ ID NO:23 and SEQ ID NO:24). In another embodiment, SEQ ID NO:24 is not included, and the analogue would be characterized as female.

In more advanced embodiments including genetic material, each sequence in SEQ ID NO:1-22 may be used as a template to make either one potentially altered sequence (homozygous locus) or two different sequences (heterozygous locus) for input into PCR. A template may be altered to produce a new allele through the insertion or deletion of single nucleotides, or dinucleotide repeats, within its motif. It is advisable to use a list of known alleles, as found in column 540, as a guide when altering a template. In even more advanced embodiments, a computer program or apparatus may be used to randomly generate genotypes under the assumption of Hardy-Weinberg equilibrium at all STR loci. In this way, each production run of synthetic horn would have a unique DNA profile, thereby making it look like different runs came from different rhinoceroses.

Other embodiments including genetic material may be based on the aforementioned DNA profiling system, but with allele frequencies collected from black rhinoceroses. Yet other embodiments may be based on entirely different DNA profiling systems. Any DNA profiling system employing loci located on either mitochondrial or nuclear DNA, and possessing STRs, Single Nucleotide Polymorphisms (SNPs), other forms of genetic variation, or combinations thereof is amenable to forgery.

In cases where a DNA profiling systems does not have published primers, fake DNA profiles can still be generated. In such embodiments, the primers may be sequenced and used to find exemplary DNA sequences in CerSimSim1.0. Alternatively, if a rhinoceros's cells are available, their DNA may be amplified by PCR using the unpublished primers or by Whole Genome Amplification (WGA) and then included in the final analogue.

In particular embodiments, powdered analogues, and in particular embodiments, powdered analogues with additives, can be formulated into compositions. Compositions intended for administration to a living animal subject (e.g., human) can include at least one pharmaceutically acceptable carrier. Pharmaceutically acceptable carriers include those that do not produce significantly adverse, allergic, or other untoward reactions that outweigh the benefit of administration. Exemplary pharmaceutically acceptable carriers and associated formulations are disclosed in Troy, D. B. and Beringer, P. (eds) Remington: The Science and Practice of Pharmacy, Lippincott; Philadelphia, 2006. 21st Edition. Compositions are prepared to meet sterility, pyrogenicity, and/or general safety and purity standards as required by relevant regulatory agencies.

Exemplary generally used pharmaceutically acceptable carriers include any and all absorption delaying agents, antioxidants, binders, buffering agents, bulking agents, chelating agents, co-solvents, coatings, coloring agents, disintegration agents, dispersion media, emulsifiers, fillers, flavoring agents, gels, isotonic agents, lubricants, perfuming agents, preservatives, releasing agents, salts, solvents, stabilizers, sweetening agents, surfactants, wetting agents, etc.

In particular embodiments, topical compositions include an analogue and a dermatological base, such as a petroleum jelly; paraffin; synthetic glyceride, mono- di- and triglyceride, wax, bentonite, carbomer, vegetable oil, animal fat, lanolin, lanolin alcohol, sorbitan ester, fatty alcohol, sulfated fatty alcohol, polysorbates, and/or polyethylene glycol (PEG). Topical compositions can be formulated as creams, lotions, salves, ointments, gels, powders, pastes, sprays, mists, aerosols, etc.

For dermatological bases that include both hydrophilic and hydrophobic reagents, emulsifying agents can be used. Exemplary anionic emulsifiers include sodium stearate, aluminum stearate, and sodium dodecyl sulfate. Exemplary cationic emulsifiers include cetyl trimethyl ammonium bromide, benzalkonium bromide and cetylpyrdinium chloride. Exemplary zwitterionic emulsifiers include phosphatidylcholine, and betaine monohydrate. Exemplary nonionic emulsifiers include PEG-30 stearate, glycerol monostearate, and glycerol monoisostearate.

Exemplary gelling agents include synthetic polyacrylic acid (carbomer), semi-synthetic cellulose derivatives (e.g., sodium carboxymethylcellulose), and xanthan. Exemplary preservatives include alkyl-4-hydroxybenzoates, sorbic acid, and benzoic acid. Exemplary antioxidants include α-tocopherol, ethyl gallate, and propyl gallate. Exemplary buffering agents include citrate buffers, succinate buffers, and tartrate buffers. Exemplary solubilizers include polysorbates, hydroxypropyl-β-cyclodextrin, and medium chain triglycerides.

For ingestion, compositions can take the form of tablets, pills, lozenges, sprays, liquids, and capsules formulated in conventional manners. Ingestible compositions can be prepared using conventional methods and materials known in the pharmaceutical art. For example, U.S. Pat. Nos. 5,215,754 and 4,374,082 relate to methods for preparing swallowable compositions. U.S. Pat. No. 6,495,177 relates to methods to prepare chewable supplements with improved mouthfeel. U.S. Pat. No. 5,965,162, relates to compositions and methods for preparing comestible units which disintegrate quickly in the mouth.

Ingestible compositions may have a shape containing no sharp edges and a smooth, uniform and substantially bubble free outer coating. Coatings of ingestible compositions can be derived from a polymeric film. Such film coatings reduce the adhesion of the compositions to the inner surface of the mouth and can aid in masking potential unpleasant tastes. Coatings can also protect the compositions from atmospheric degradation. Exemplary polymeric films include vinyl polymers, cellulosics, acrylates and methacrylates, natural gums and resins such as zein, gelatin, shellac and acacia. Other common excipients used in ingestible compositions include sucrose, fructose, lactose, glucose, lycasin, xylitol, lactitol, erythritol, mannitol, isomaltose, dextrose, polydextrose, dextrin, compressible cellulose, compressible honey, compressible molasses, fondant or gums, vegetable oils, animal oils, alkyl polysiloxanes, corn starch, potato starch, pre-gelatinized starches, stearic acid, calcium stearate, magnesium stearate, zinc stearate, benzoic acid, and colorants For administration by inhalation (e.g., nasal or pulmonary), the compositions can be formulated as aerosol sprays for pressurized packs or a nebulizer, with the use of suitable propellants, e.g. dichlorodifluoromethane, trichlorofluoromethane, or dichlorotetra-fluoroethane.

Fillers and excipients are commercially available from companies such as Aldrich Chemical Co., FMC Corp, Bayer, BASF, Alexi Fres, Witco, Mallinckrodt, Rhodia, ISP, and others.

The amount and concentration of an analogue in a composition can be selected based on relevant factors such as the solubility of analogue in a carrier, the potency and activity of the analogue, and the manner of administration of the composition. Compositions will generally include from 0.0001 to 99 wt. %, of the analogue by weight of the total composition.

Compositions of the disclosure including a safe and effective amount of an analogue, optionally with an additive, can be packaged into various containers. In particular embodiments, the compositions are packaged within containers described and claimed in U.S. Design Pat. Application No. 29/529,808 filed Jun. 10, 2015.

Example 1

1 part of hydrolyzed keratin obtained from sheep's wool with a pH of 5-5.5 and a molecular weight of 3,500-4,500 daltons was reacted with 3 parts of calcium hydroxide for 12-48 hours at 40-50° C. under a nitrogen atmosphere (Thyagarajan et al. "Scope of Poultry Waste Utilization." *IOSR-JAVS*. 2013; No. 6, Vol. 5:29-35). This was done to discourage the premature formation of disulfide bonds due to reaction with air. Over the course of the reaction, ammonia gas was created as a by-product and allowed to escape. It should be noted that keratin derived from genetically modified yeast may be used in place of hydrolyzed keratin obtained from sheep's wool.

The resultant slurry, containing polymerized keratin rich in β-sheets 100, as shown in FIG. 1, was then removed from the nitrogen atmosphere. It was subsequently dried in a drying oven at 70-90° C. until the moisture content was below 1% as measured by a Karl Fischer titrator. β-sheets 100 were chosen as the base structure in the present embodiment because key proteins could be entrapped between them to allow for a greater compositional match to authentic horn.

The dried powder was then dissolved in a potassium phosphate buffer solution and the following were added by mass (it should be noted that this is the native composition present in northern white rhinoceros horn): 2% arginine; 5% lysine; 9% cholesterol; 3% taurine; 0.2% hexosamines (fructosamine & glucosamine); and 0.2% sphingosine. The variance of the above percentages can be as much as ±20% of the reported values since values in a wild rhinoceros horn will vary based on diet.

Figure 2:
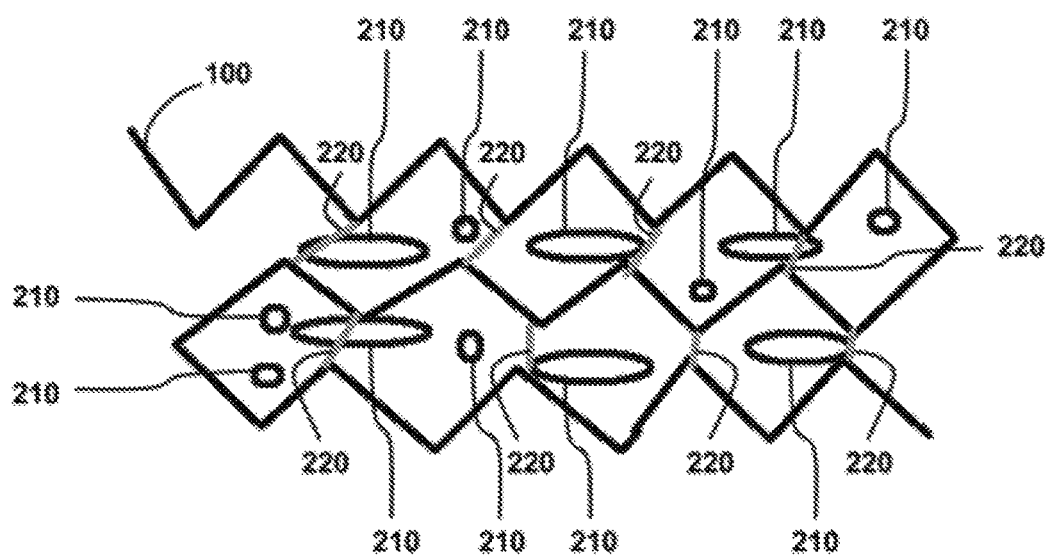
FIG. 2 is a schematic diagram illustrating how a β-sheet, as shown in FIG. 1, may change conformation to entrap a plurality of chemical additives.

Once the above additives 210, as illustrated in FIG. 2, were mixed well with the keratin base, ½ part of 20-50% hydrogen peroxide was added to encourage disulfide/hydrogen bond 220 formation in the β-sheets 100, thereby entrapping the above additives 210. Prior to this step, the β-sheets 100 were of relatively small size and had a limited number of disulfide bonds. The powder was then dried again in a drying oven at 70-90° C. until the moisture content was below 1% as measured by a Karl Fischer titrator.

It should be noted that, in the present embodiment, any alkaline solution would work as a replacement for calcium hydroxide such as sodium hydroxide; however, another calcium source would then need to be added in order to match the calcium levels in authentic horn which vary from 6%-8% of the total organics present. Additionally, other non-reactive atmospheres besides nitrogen may be used, such as argon, and other keratin sources of varying molecular size may be used, such as digested bird's feathers. Other solutions may be used in the place of hydrogen peroxide, such as nitric acid, as long as they aid in the oxidation of the keratin sulfhydryl groups.

Figure 3:
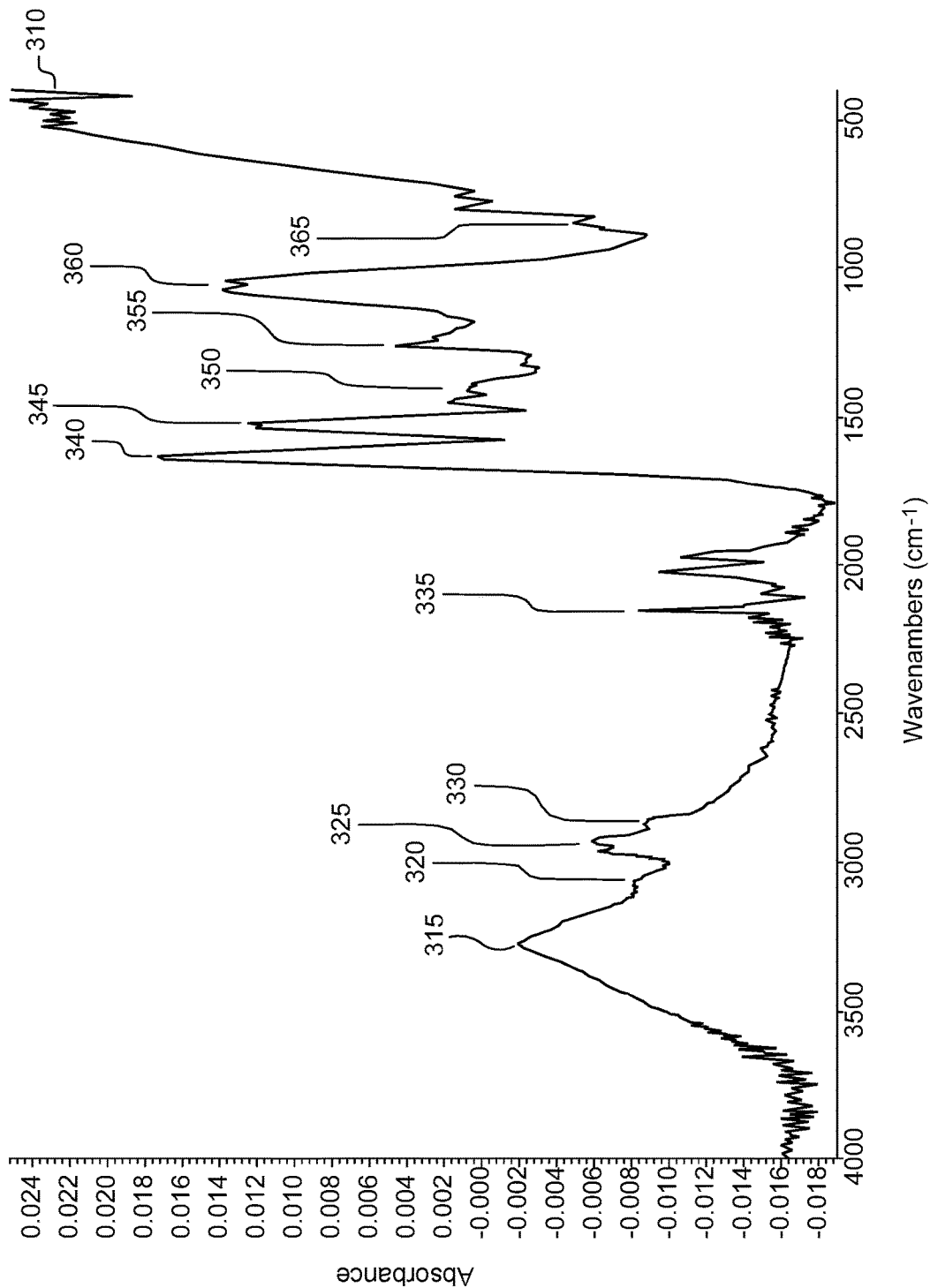
FIG. 3 is a FTIR spectrograph of a rhinoceros horn analogue produced in accordance synthesis methods disclosed herein.

Turning now to FIG. 3, there is shown a sample spectrum 310 of a rhinoceros horn analogue synthesized in accordance with the present embodiment. The following features are of note:

a. 315 at 3250 $cm^{-1}$, belonging to O—H stretching vibrations of cholesterol;
b. 320 at 3050 $cm^{-1}$, belonging to N—H stretching vibrations of primary amines;
c. 325 at 2900 $cm^{-1}$, belonging to C—H asymmetric stretching vibrations of hydrocarbons;
d. 330 at 2850 $cm^{-1}$, belonging to C—H symmetric stretching vibrations of hydrocarbons;
e. 335 at 2300 $cm^{-1}$, belonging to P—H stretching vibrations of phospholipids;
f. 340 at 1650 $cm^{-1}$, belonging to C=O stretching vibrations of amino acids;
g. 345 at 1550 $cm^{-1}$, belonging to N—H bending vibrations of primary amines;
h. 350 at 1400 $cm^{-1}$, belonging to C—H bending vibrations of hydrocarbons;
i. 355 at 1200 $cm^{-1}$, belonging to P=O stretching vibrations of phospholipids;
j. 360 at 1050 $cm^{-1}$, belonging to S=O stretching vibrations of taurine;
k. 365 at 880 $cm^{-1}$, belonging to S—O stretching vibrations of taurine.

The above features of note may have peak variances of up to 40 $cm^{-1}$ due to instrument calibration and sampling methods.

Figure 4:
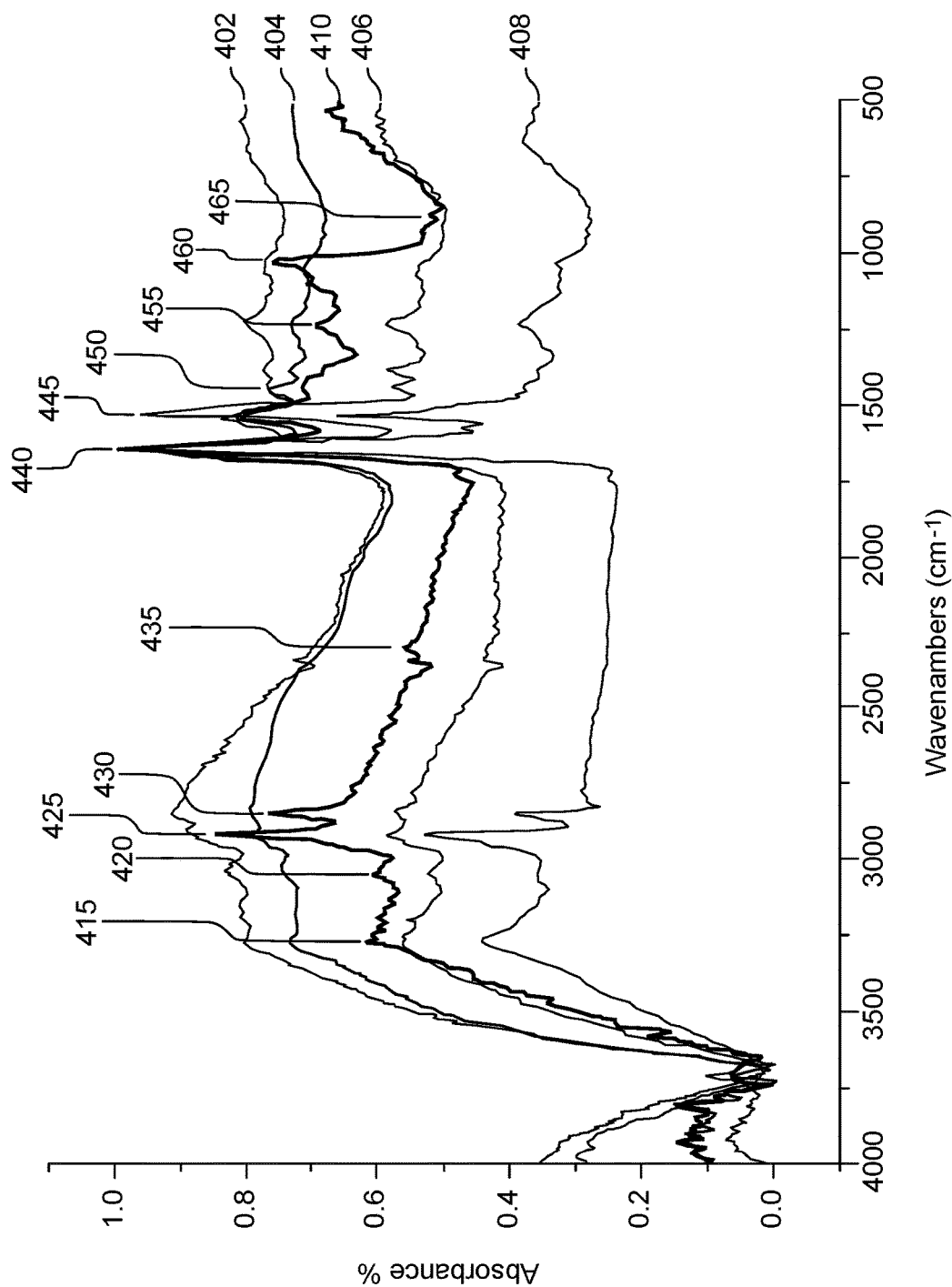
FIG. 4 contains FTIR spectra of the horns of several animals, for reference purposes.

Referring now to FIG. 4, there are shown reference spectra of cattle horn 402, goat horn 404, sheep horn 406, yak horn 408, and rhinoceros horn 410 reported elsewhere (Shengqing et al. "Identification of Rhinoceros Horn and Its Substitutes." Adv. Mat. Res. 2011; Vol. 177:636-639). Still referring to FIG. 4, as well as to FIG. 3, there is a correspondence of 315 with 415, 320 with 420, 325 with 425, 330 with 430, 335 with 435, 340 with 440, 345 with 445, 350 with 450, 355 with 455, 360 with 460, and 365 with 465. Discrepancies between the spectra are most likely due to the fact that Attenuated Total Reflection (ATR), a sampling technique which enables samples to be examined without special preparation, was used in the generation of the sample spectrum 310 but not the reference spectrum 410. In general, ATR allows for higher spatial resolution imaging. This explains why the peaks in the sample spectrum 310 are slightly sharper, particularly at the lower wavelengths. Likewise, the cluster of peaks around 2000 cm$^{-1}$ in the sample spectrum 310 are vibrations from aromatics, and are much more prominent on a diamond ATR. Nonetheless, the sample spectrum 310 has both a taurine peak 360 and phospholipid peak 335. Specifically, the presence taurine and phospholipid peaks are the defining peaks that differentiate rhinoceros horn from other horns. It is of note that due to resolution differences between instruments and sampling methods, the peaks present and listed above can have a variance of up±1-40 cm$^{-1}$.

In some embodiments, the keratin base may mainly include α-helices. These embodiments would differ from the aforementioned embodiment in that the initial digestion with calcium hydroxide would be performed in air instead of nitrogen.

In terms of physical properties, the rhinoceros horn analog had a Shore A hardness of 92-96, a Shore D hardness of 68-72, and a Density of 1.122-2.222 g/cubic cm. This matches that of wild rhinoceros. Additionally, the total inorganic content of the rhinoceros horn analog matched that of wild rhinoceros horn with: 66-70% sulfur; 15-19% potassium; 5-9% calcium; 0-3% iron; 0.2-0.4% titanium; and 0-4% zinc.

In some embodiments, the keratin used in the rhinoceros horn analogue may be derived from other sources besides wool. One such source would be a recombinant protein secreted from genetically modified yeast. Exemplary keratin proteins that may be used are shown in FIG. 6 where 610 is the SEQ ID NO, and 620 is the amino acid sequence for the hard keratin.

The disclosure is not limited to the particular nucleotide and protein sequences disclosed herein (e.g., SEQ ID NOs. 1-43), but rather includes variants and modifications of these sequences. "Variants" include sequences having one or more additions, deletions, stop positions, or substitutions, as compared to a sequence disclosed elsewhere herein.

Variants included within nucleotide sequences account for degeneracy of the genetic code, allelic variants, and homologous sequences between species.

Variants included within protein sequences account for conservative or non-conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the protein backbone in the area of the alteration (e.g., the α-helical or β-sheet structure); the charge or hydrophobicity of the molecule at the target site; or the bulk of the side chain. Non-conservative substitutions which in general are expected to produce the greatest changes in the proteins's properties are those in which (i) a hydrophilic residue (e.g. S or T) can be substituted for (or by) a hydrophobic residue (e.g. L, I, F, V, or A); (ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of sequences disclosed herein also include sequences with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a sequence disclosed herein.

"Percent (%) sequence identity" with respect to the sequences identified herein is defined as the percentage of nucleotide or amino acid residues in a candidate sequence that are identical with the nucleotide or amino acid residues in the reference sequence after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

Variants will typically exhibit the same qualitative biological activity as a reference sequence, although variants can be selected to modify the characteristics of a reference sequence as needed. Screening of variants can be performed using assays known to those of ordinary skill in the art.

Covalent modifications of proteins are also included within the scope of the disclosure. One type of covalent modification includes reacting targeted amino acid residues of proteins with an organic derivatizing agent that is capable of reacting with selected side chains or the N- or C-terminal residues of proteins. Derivatization with bifunctional agents can be useful, for instance, for crosslinking proteins to a water-insoluble support matrix or surface, or for stability. Commonly used crosslinking agents include 1,1-bis(diazoacetyl)-2-phenylethane, glutaraldehyde, N-hydroxysuccinimide esters (e.g., esters with 4-azidosalicylic acid), homobifunctional imidoesters, including disuccinimidyl esters (e.g., 3,3'-dithiobis(succinim idylpropionate), bifunctional maleim ides (e.g., bis-N-maleimido-1,8-octane) and agents such as methyl-3-((p-azidophenyl)dithio)propioimidate, and 1-ethyl-3-(-3-dimethylaminopropyl)carbodiimide hydrochloride.

Other modifications include deamidation of glutaminyl and asparaginyl residues to the corresponding glutamyl and aspartyl residues, respectively, hydroxylation of P and L, phosphorylation of hydroxyl groups of S or T residues, methylation of the amino groups of L, R, and H side chains (see, e.g., T. E. Creighton, Proteins: Structure and Molecular Properties, W.H. Freeman & Co., San Francisco, pp. 79-86 (1983)), acetylation of the N-terminal amine, and/or amidation of any C-terminal carboxyl group. In addition, modifications such as derivitization with polyethylene glycols (and other glycols) to increase stability are also included.

Another modification within the scope of the disclosure is to employ glycosylated amino acid residues (e.g. S, T or N residues), singly or in combination. Glycosylation, which may be carried out using standard conditions, may be used to enhance solubility, alter pharmacokinetics and pharmacodynamics or to enhance binding via a specific or nonspecific interaction involving the glycosidic moiety. In another approach glycosylated amino acids such as O-(2-acetamido-2-deoxy-3,4,6-tri-O-acetyl-β-D-glucopyranosyl) S or the analogous T derivative (either the D- or L-amino acids) may be incorporated into the protein during manual or automated solid phase protein synthesis, or in manual or automated solution phase protein synthesis. Similarly D- or L-$N^Y$-(2-acetamido-2-deoxy-3,4,6-tri-O-acetyl-β-D-glucopyr-anosyl)-N can be employed. The use of amino acids glycosylated on a pendant oxygen, nitrogen or sulfur function by the agency of suitably functionalized and activated carbohydrate moieties that can be employed in glycosylation is anticipated. Such carbohydrate functions could be monosaccharides, disaccharides or even larger assemblies of oligosaccharides (Kihlberg, January (2000) Glycopeptide synthesis. In: Fmoc Solid Phase Peptide Synthesis—A Practical Approach (Chan, W. C. and White, P. D. Eds) Oxford University Press, New York, N.Y. Chap. 8, pp 195-213).

Also anticipated is the appendage of carbohydrate functions to amino acids by means other than glycosylation via activation of a leaving group at the anomeric carbon. Linkage of the amino acid to the glycoside is not limited to the formation of a bond to the anomeric carbon of the carbohydrate function. Instead, linkage of the carbohydrate moiety to the amino acid could be through any suitable, sufficiently reactive oxygen atom, nitrogen atom, carbon atom or other pendant atom of the carbohydrate function via methods employed for formation of C-heteroatom, C—C or heteroatom-heteroatom (examples are S—S, O—N, N—N, P—O, P—N) bonds known in the art.

EXEMPLARY EMBODIMENTS

1. A synthetic rhinoceros horn analogue wherein the synthetic rhinoceros horn analogue matches at least two characteristics of natural rhinoceros horn selected from:
   a. an Attenuated Total Reflection (ATR) spectra with a taurine peak at 1050 $cm^{-1}$±1-40 $cm^{-1}$ and a phospholipid peak at 2300 $cm^{-1}$±1-40 $cm^{-1}$;
   b. an Attenuated Total Reflection (ATR) spectra with a cholesterol peak at 3250 $cm^{-1}$±1-40 $cm^{-1}$; a primary amine peak at 3050 $cm^{-1}$±1-40 $cm^{-1}$; a hydrocarbon peak at 2900 $cm^{-1}$±1-40 $cm^{-1}$; a hydrocarbon peak at 2850 $cm^{-1}$±1-40 $cm^{-1}$; a phospholipid peak at 2300 $cm^{-1}$±1-40 $cm^{-1}$, an amino acid peak at 1650 $cm^{-1}$±1-40 $cm^{-1}$; a primary amine peak at 1550 $cm^{-1}$±1-40 $cm^{-1}$; a hydrocarbon peak at 1400 $cm^{-1}$±1-40 $cm^{-1}$; a phospholipid peak at 1200 $cm^{-1}$±1-40 $cm^{-1}$; a taurine peak at 1050 $cm^{-1}$±1-40 $cm^{-1}$; and a taurine peak at 880 $cm^{-1}$±1-40 $cm^{-1}$;
   c. a Shore A hardness of 92-96;
   d. a Shore D hardness of 68-72;
   e. a Density of 1.122-2.222 g/cubic cm;
   f. inorganic content of 66-70% sulfur; 15-19% potassium; 5-9% calcium; 0-3% iron; 0.2-0.4% titanium; and 0-4% zinc; and
   g. organic content of 1.6%-2.4% arginine; 4-6% lysine; 7.2-10.8% cholesterol; 2.75-3.25% taurine; 0%-1.25% hexosamines; and 0.1%-0.3% sphingosine.
2. A synthetic rhinoceros horn analogue of embodiment 1 matching all of characteristics a., b., c., d., e., f., and g.
3. A synthetic rhinoceros horn analogue of embodiment 1 matching characteristics (i) a., f., and g. or (ii) a. b., f., and g.
4. A synthetic rhinoceros horn analogue of any of embodiments 1-3 in solid form.
5. A synthetic rhinoceros horn analogue of embodiment 1 or 3 in powder form.
6. A synthetic rhinoceros horn analogue of any of embodiments 1-5 formulated into a composition.
7. A synthetic rhinoceros horn analogue of embodiment 6 wherein the composition is formulated for topical application.
8. A synthetic rhinoceros horn analogue of any of embodiments 1, 3, or 5-7 in powder form packaged in a container depicted in U.S. Design Pat. Application No. 29/529,808 filed Jun. 10, 2015.
9. A synthetic rhinoceros horn analogue of any of embodiments 1-8 formulated into a composition and packaged in a container depicted in U.S. Design Pat. Application No. 29/529,808 filed Jun. 10, 2015.
10. A synthetic rhinoceros horn analogue of any of embodiments 1-9 comprising a medicinal or genetic additive.
11. A synthetic rhinoceros horn analogue of embodiment 10 wherein the additive is a medicinal additive selected from caffeine, aspirin, acetaminophen, ibuprofen, sildenafil, tadalafil, or combinations thereof.
12. A synthetic rhinoceros horn analogue of embodiment 10 or 11 wherein the additive is a genetic additive selected from SEQ ID NOs. 1-24.
13. A synthetic rhinoceros horn analogue of any of embodiments 1-12 wherein the synthetic rhinoceros horn analogue has a keratin base.
14. A synthetic rhinoceros horn analogue of embodiment 13 wherein the keratin of the keratin base is obtained from wool, bird feathers, or genetically-modified yeast.
15. A synthetic rhinoceros horn analogue of embodiment 13 or 14 wherein the keratin of the keratin base has a sequence selected from SEQ ID NOs. 25-43.
16. A composition comprising a synthetic rhinoceros horn analogue.
17. A composition of embodiment 16 wherein the composition is formulated for topical application, ingestion or inhalation.
18. A method of synthesizing a synthetic rhinoceros horn analogue comprising trapping organic compounds in a keratin base.

19. A method of embodiment 18 wherein trapping comprises:
   a. mixing polymerized keratin with the organic compounds in a buffer solution;
   b. adding a second solution to the mixed polymerized keratin and organic compounds to aid in oxidation of keratin sulfhydryl groups; and
   c. drying the mixture to a moisture content below 1% as measured by a Karl Fischer titrator.
20. A method of embodiment 19 wherein the polymerized keratin comprises β-sheets.
21. A method of embodiment 19 or 20 wherein the buffer solution is a potassium phosphate buffer solution.
22. A method of any of embodiments 19-21 wherein the second solution is hydrogen peroxide or nitric acid.
23. A method of any of embodiments 18-22 wherein the organic compounds include arginine; lysine; cholesterol; taurine; hexosamines, and sphingosine.
24. A method of embodiment 23 wherein the organic compounds include 1.6%-2.4% arginine; 4-6% lysine; 7.2-10.8% cholesterol; 2.75-3.25% taurine; 0.1%-1.25% hexosamines; and 0.1%-0.3% sphingosine.
25. A method of any of embodiments 19-24 further comprising in step a. or step b. adding a medicinal additive, a genetic additive or a medicinal and a genetic additive.
26. A method of embodiment 25 wherein the additive is a medicinal additive selected from caffeine, aspirin, acetaminophen, ibuprofen, sildenafil, tadalafil, or combinations thereof.
27. A method of embodiment 25 or 26 wherein the additive is a genetic additive selected from SEQ ID NOs. 1-24.
28. A method of any of embodiments 19-27 further comprising, before the mixing, placing keratin in an alkaline solution under a non-reactive atmosphere.
29. A method of embodiment 28 wherein the alkaline solution is calcium hydroxide or sodium hydroxide.
30. A method of embodiment 28 or 29 wherein the non-reactive atmosphere is a nitrogen atmosphere or an argon atmosphere.
31. A method of any of embodiments 28-30 wherein the keratin remains in the alkaline solution for 12-48 hours at 40-50° C.
32. A method of any of embodiments 28-31 wherein the keratin has a pH of 5-5.5.
33. A method of any of embodiments 28-32 wherein the keratin has a molecular weight of 3,500-4,500 daltons.
34. A synthetic rhinoceros horn analogue wherein the synthetic rhinoceros horn analogue matches at least three characteristics of natural rhinoceros horn selected from hardness, density, surface morphology, color, texture, rate of decay, brittleness, tensile strength, optical representation, presence and percentage of organic components, and presence and percentage of inorganic components wherein a match is defined as a difference in characteristic measurement between the synthetic rhinoceros horn analogue and the natural rhinoceros horn of 20% or less.
35. A synthetic rhinoceros horn analogue of embodiment 34 wherein the difference in characteristic measurement between the synthetic rhinoceros horn analogue and the natural rhinoceros horn is 15% or less, 10% or less; 5% or less; 3% or less or 1% or less.
36. A synthetic rhinoceros horn analogue of embodiment 34 or 35 in solid form.
37. A synthetic rhinoceros horn analogue of embodiment 34 or 35 in powder form.
38. A synthetic rhinoceros horn analogue of any of embodiments 34-37 formulated into a composition.
39. A synthetic rhinoceros horn analogue of embodiment 38 wherein the composition is formulated for topical application.
40. A synthetic rhinoceros horn analogue of any of embodiments 34, 35, or 37-39 in powder form packaged in a container depicted in U.S. Design Pat. Application No. 29/529,808 filed Jun. 10, 2015.
41. A synthetic rhinoceros horn analogue of any of embodiments 34-40 formulated into a composition and packaged in a container depicted in U.S. Design Pat. Application No. 29/529,808 filed Jun. 10, 2015.
42. A synthetic rhinoceros horn analogue of any of embodiments 34-41 comprising a medicinal or genetic additive.
43. A synthetic rhinoceros horn analogue of embodiment 42 wherein the additive is a medicinal additive selected from caffeine, aspirin, acetaminophen, ibuprofen, sildenafil, tadalafil, or combinations thereof.
44. A synthetic rhinoceros horn analogue of embodiment 42 or 43 wherein the additive is a genetic additive selected from SEQ ID NOs. 1-24.
45. A synthetic rhinoceros horn analogue of any of embodiments 34-44 wherein the synthetic rhinoceros horn analogue has a keratin base.
46. A synthetic rhinoceros horn analogue of embodiment 45 wherein the keratin of the keratin base is obtained from wool, bird feathers, or genetically-modified yeast.
47. A synthetic rhinoceros horn analogue of embodiment 45 or 46 wherein the keratin of the keratin base has a sequence selected from SEQ ID NOs. 25-43.
48. A synthetic rhinoceros horn analogue of embodiment 34 wherein the measured characteristics reflect at least two of:
   a. an Attenuated Total Reflection (ATR) spectra with a taurine peak at $1050$ $cm^{-1}\pm 1$-$40$ $cm^{-1}$ and a phospholipid peak at $2300$ $cm^{-1}\pm 1$-$40$ $cm^{-1}$;
   b. an Attenuated Total Reflection (ATR) spectra with a cholesterol peak at $3250$ $cm^{-1}\pm 1$-$40$ $cm^{-1}$; a primary amine peak at $3050$ $cm^{-1}\pm 1$-$40$ $cm^{-1}$; a hydrocarbon peak at $2900$ $cm^{-1}\pm 1$-$40$ $cm^{-1}$; a hydrocarbon peak at $2850$ $cm^{-1}\pm 1$-$40$ $cm^{-1}$; a phospholipid peak at $2300$ $cm^{-1}\pm 1$-$40$ $cm^{-1}$, an amino acid peak at $1650$ $cm^{-1}\pm 1$-$40$ $cm^{-1}$; a primary amine peak at $1550$ $cm^{-1}\pm 1$-$40$ $cm^{-1}$; a hydrocarbon peak at $1400$ $cm^{-1}\pm 1$-$40$ $cm^{-1}$; a phospholipid peak at $1200$ $cm^{-1}\pm 1$-$40$ $cm^{-1}$; a taurine peak at $1050$ $cm^{-1}\pm 1$-$40$ $cm^{-1}$; and a taurine peak at $880$ $cm^{-1}\pm 1$-$40$ $cm^{-1}$;
   c. a Shore A hardness of 92-96;
   d. a Shore D hardness of 68-72;
   e. a Density of 1.122-1.222 g/cubic cm;
   f. inorganic content of 66-70% sulfur; 15-19% potassium; 5-9% calcium; 0-3% iron; 0.2-0.4% titanium; and 0-4% zinc; and
   g. organic content of 1.6%-2.4% arginine; 4-6% lysine; 7.2-10.8% cholesterol; 2.75-3.25% taurine; 0%-1.25% hexosamines; and 0.1%-0.3% sphingosine.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a synthetically-created substance not to match a spectra from a natural rhinoceros horn with a 1-40 $cm^{-1}$ peak deviation range.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range.

Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A synthetic rhinoceros horn analogue comprising:
a keratin base, arginine, lysine, cholesterol, taurine, hexosamines, sphingosine, sulfur, potassium, calcium, iron, titanium, zinc, and genetic material comprising amplifiable forensic loci selected from SEQ ID NOs. 1-23 or SEQ ID NOs. 1-24, wherein at least one of the loci comprises a substitution, insertion, or deletion that is absent from natural rhinoceros horn,
wherein the synthetic rhinoceros horn analogue matches at least two characteristics of natural rhinoceros horn selected from:

a. an Attenuated Total Reflection (ATR) spectra with a taurine peak at 1050 cm−1±1-40 cm−1 and a phospholipid peak at 2300 cm−1±1-40 cm−1;
b. an Attenuated Total Reflection (ATR) spectra with a cholesterol peak at 3250 cm−1±1-40 cm−1; a primary amine peak at 3050 cm−1±1-40 cm−1; a hydrocarbon peak at 2900 cm−1±1-40 cm−1; a hydrocarbon peak at 2850 cm−1±1-40 cm−1; a phospholipid peak at 2300 cm−1±1-40 cm−1, an amino acid peak at 1650 cm−1±1-40 cm−1; a primary amine peak at 1550 cm−1±1-40 cm−1; a hydrocarbon peak at 1400 cm−1±1-40 cm−1; a phospholipid peak at 1200 cm−1±1-40 cm−1; a taurine peak at 1050 cm−1±1-40 cm−1; and a taurine peak at 880 cm−1±1-40 cm−1;
c. a Shore A hardness of 92-96;
d. a Shore D hardness of 68-72;
e. a Density of 1.122-2.222 g/cubic cm;
f. inorganic content of 66-70% sulfur; 15-19% potassium; 5-9% calcium; 0-3% iron; 0.2-0.4% titanium; and 0-4% zinc; and
g. organic content of 1.6%-2.4% arginine; 4-6% lysine; 7.2-10.8% cholesterol; 2.75-3.25% taurine; 0%-1.25% hexosamines; and 0.1%-0.3% sphingosine.

2. A synthetic rhinoceros horn analogue of claim 1 matching all of characteristics a., b., c., d., e., f., and g.

3. A synthetic rhinoceros horn analogue of claim 1 matching characteristics (i) a., f., and g. or (ii) a. b., f., and g.

4. A synthetic rhinoceros horn analogue of claim 1 in solid form.

5. A synthetic rhinoceros horn analogue of claim 3 in powder form.

6. A synthetic rhinoceros horn analogue of claim 5 formulated into a composition.

7. A synthetic rhinoceros horn analogue of claim 6 wherein the composition is formulated for topical application and comprises petroleum jelly, paraffin, synthetic glyceride, monoglyceride, diglyceride, triglyceride, wax, bentonite, carbomer, vegetable oil, animal fat, lanolin, lanolin alcohol, sorbitan ester, fatty alcohol, sulfated fatty alcohol, polysorbates, polyethylene glycol, or a combination thereof.

8. A synthetic rhinoceros horn analogue of claim 1 further comprising a medicinal additive.

9. A synthetic rhinoceros horn analogue of claim 8 wherein the medicinal additive is selected from caffeine, aspirin, acetaminophen, ibuprofen, sildenafil, tadalafil, or combinations thereof.

10. A synthetic rhinoceros horn analogue of claim 1 further comprising at least one wherein the amplifiable forensic loci consist of selected from SEQ ID NOs. 1-23 or SEQ ID NOs. 1-24.

11. A synthetic rhinoceros horn analogue of claim 1 wherein the keratin of the keratin base is obtained from wool, bird feathers, or genetically-modified yeast.

12. A synthetic rhinoceros horn analogue of claim 1 wherein the keratin of the keratin base has a sequence selected from SEQ ID NOs. 25-43.

13. A method of synthesizing a synthetic rhinoceros horn analogue comprising trapping organic compounds in a keratin base wherein the trapping comprises:
a. mixing polymerized keratin with the organic compounds in a buffer solution;
b. adding a second solution to the mixed polymerized keratin and organic compounds to aid in oxidation of keratin sulfhydryl groups; and
c. drying the mixture to a moisture content below 1% as measured by a Karl Fischer titrator.

14. A method of claim 13 wherein the polymerized keratin comprises β-sheets; the buffer solution is a potassium phosphate buffer solution; the second solution is hydrogen peroxide or nitric acid; and the organic compounds include arginine; lysine; cholesterol; taurine; hexosamines, and sphingosine.

15. A synthetic rhinoceros horn analogue of claim 1 comprising 1.6-2.4% arginine; 4-6% lysine; 7.2-10.8% cholesterol; 2.75-3.25% taurine; 0.2-1.25% hexosamines; and 0.1-0.3% sphingosine.

16. A synthetic rhinoceros horn analogue of claim 1 comprising 66-70% sulfur, 15-19% potassium, 5-9% calcium, and 0.2-0.4% titanium.

17. A synthetic rhinoceros horn analogue comprising:
a keratin base, arginine, lysine, cholesterol, taurine, hexosamines, sphingosine, sulfur, potassium, calcium, iron, titanium, zinc, and a DNA watermark comprising a genetic sequence that is absent from natural rhinoceros horn,
wherein the synthetic rhinoceros horn analogue matches at least two characteristics of natural rhinoceros horn selected from:
d. an Attenuated Total Reflection (ATR) spectra with a taurine peak at 1050 cm−1±1-40 cm−1 and a phospholipid peak at 2300 cm−1±1-40 cm−1;
e. an Attenuated Total Reflection (ATR) spectra with a cholesterol peak at 3250 cm−1±1-40 cm−1; a primary amine peak at 3050 cm−1±1-40 cm−1; a hydrocarbon peak at 2900 cm−1±1-40 cm−1; a hydrocarbon peak at 2850 cm−1±1-40 cm-1; a phospholipid peak at 2300 cm−1±1-40 cm−1, an amino acid peak at 1650 cm−1±1-40 cm−1; a primary amine peak at 1550 cm−1±1-40 cm−1; a hydrocarbon peak at 1400 cm−1±1-40 cm−1; a phospholipid peak at 1200 cm−1±1-40 cm−1; a taurine peak at 1050 cm−1±1-40 cm−1; and a taurine peak at 880 cm−1±1-40 cm−1;
f. a Shore A hardness of 92-96;
g. a Shore D hardness of 68-72;
h. a Density of 1.122-2.222 g/cubic cm;
i. inorganic content of 66-70% sulfur; 15-19% potassium; 5-9% calcium; 0-3% iron; 0.2-0.4% titanium; and 0-4% zinc; and
j. organic content of 1.6%-2.4% arginine; 4-6% lysine; 7.2-10.8% cholesterol; 2.75-3.25% taurine; 0%-1.25% hexosamines; and 0.1%-0.3% sphingosine.

* * * * *

SEQUENCE LISTING

<160> NUMBER OF SEQ ID NOS: 43

<210> SEQ ID NO 1
<211> LENGTH: 242
<212> TYPE: DNA
<213> ORGANISM: Rhinoceros unicornis

<400> SEQUENCE: 1

| gatcagtaac accaaaatcc gtgtgtgtgt gtgtgtgtgt gtgtgtgcat gtgtgtaggc | 60 |
| agggggacat tggtcacaac taacacatga aggaatgaga aaatcccatg ttgagttgaa | 120 |
| cagtaatagg gtatacaaca atttctaata ttgcatttgg ataatgctag tcttgatttc | 180 |
| tttttgttgt atattttcca tttttctcat attatgtcct tggtgatcct tctgtcttca | 240 |
| ct | 242 |

<210> SEQ ID NO 2
<211> LENGTH: 138
<212> TYPE: DNA
<213> ORGANISM: Rhinoceros unicornis

<400> SEQUENCE: 2

| agattcttgg aaaggtcact caaggcacac agaaaatgcc tcctacacac acacacacac | 60 |
| acacacacgc gcacacacac acatacacac gcacacacac ctgacagcac atgttctcct | 120 |
| gaggtgaaac ccaatgtt | 138 |

<210> SEQ ID NO 3
<211> LENGTH: 243
<212> TYPE: DNA
<213> ORGANISM: Rhinoceros unicornis

<400> SEQUENCE: 3

| acatgtgtaa acttgggaac tgttgttagt catgtttctc cactcagaat gagaaacgga | 60 |
| gaaatccaga atgcagaaat agaaacgact gaagcagaaa gacacaaaat gtgtgtgtgt | 120 |
| gcatgtgtgt gtgtgtgtgt gtgtgtgtgt gtgtgtgaga gagagagaga aagagggaga | 180 |
| gagagaggga gagagagatt ggaagtgggt gggattaagt agggagaaga gatcaatgaa | 240 |
| cca | 243 |

<210> SEQ ID NO 4
<211> LENGTH: 134
<212> TYPE: DNA
<213> ORGANISM: Rhinoceros unicornis

<400> SEQUENCE: 4

| tcatttctct gttccccata gcacaaagtg gggctcagaa aatatttgat ctcacacaca | 60 |
| cacacacaca cacacacaca catttacatg cattagtgct aacatcttat ccttcacata | 120 |
| tcgtggatat tgct | 134 |

<210> SEQ ID NO 5
<211> LENGTH: 159
<212> TYPE: DNA
<213> ORGANISM: Rhinoceros unicornis

<400> SEQUENCE: 5

| taagtcacag ggactaatct gtaaaattga gataataata ggaccctgct cccaacacac | 60 |
| acacacacac acacacacac acacacttca gtgggttgtt atgaccacca gatgagacaa | 120 |
| tatatgtaaa atactttgcc tcattcacaa taaaccctc | 159 |

<210> SEQ ID NO 6
<211> LENGTH: 238
<212> TYPE: DNA
<213> ORGANISM: Rhinoceros unicornis

<400> SEQUENCE: 6

| | | | | | |
|---|---|---|---|---|---|
| atcttcctca | gcaataaggg | gaggattagc | aacggatgtt | agctcagggc taatcttcct | 60 |
| cacacacaca | caaaaattca | ttataaattt | aactcttaga | gtaaaaactc ttcattctcc | 120 |
| ttcagtccct | agaggaattg | agaaatagtc | ccaaactcag | tggcagagaa tcaagtttag | 180 |
| aatatgaaaa | atgtctagca | aaattactct | tttacacaga | actggaaact ctgatgat | 238 |

<210> SEQ ID NO 7
<211> LENGTH: 215
<212> TYPE: DNA
<213> ORGANISM: Rhinoceros unicornis

<400> SEQUENCE: 7

| | | | | | |
|---|---|---|---|---|---|
| agggtggaat | gtcaagtagc | ggggctgata | ttttccacgt | ttccagtttc tttaatttgc | 60 |
| ctgtggctga | gctggcgctg | ggagccccac | ctccattctg | tgtgtgcctg tgtgtgtgtg | 120 |
| tgtgtgtgtg | tgtgtgtgtg | tgtgtgttgg | aaggtggcag | aggcaggggt ggggcaacaa | 180 |
| gctgggggca | gggactccta | gtctccctct | agaag | | 215 |

<210> SEQ ID NO 8
<211> LENGTH: 222
<212> TYPE: DNA
<213> ORGANISM: Rhinoceros unicornis

<400> SEQUENCE: 8

| | | | | | |
|---|---|---|---|---|---|
| catgtgaaat | ggaccgtcag | gcattggcag | gaagcagctt | ggaggtttcc acgggacgcg | 60 |
| tagctcctgg | cttggcaggt | gtggtggctt | gtgtatgtga | tagcagcgcg cacacacaca | 120 |
| cgcgcgcaca | cacacacaca | cacacacaca | cgagccaggg | gcatccccac ttaccctggg | 180 |
| ctcttttgga | aatatccatg | cccccctgccc | cttcccagaa at | | 222 |

<210> SEQ ID NO 9
<211> LENGTH: 198
<212> TYPE: DNA
<213> ORGANISM: Rhinoceros unicornis

<400> SEQUENCE: 9

| | | | | | |
|---|---|---|---|---|---|
| ccaggtgaag | ggtcttatat | ttagcaagct | atctatatta | ggatatgtgg agggaaattt | 60 |
| tcttttttat | tgttttgaca | tatttggcat | tttatccttt | tgcgctattt ttttttgtgt | 120 |
| gtgtgtgtgt | gtgtgtgtgt | atgtgtgtgt | gtgtgtgtgt | gaggaagatc agccctgagg | 180 |
| taacatccat | gccaatcc | | | | 198 |

<210> SEQ ID NO 10
<211> LENGTH: 137
<212> TYPE: DNA
<213> ORGANISM: Rhinoceros unicornis

<400> SEQUENCE: 10

| | | | | | |
|---|---|---|---|---|---|
| cagtgaggaa | gattggttgc | aataaactta | ggtaaataaa | ttatcaaata tttaaaaaat | 60 |
| tgcatggaac | tacacacaca | cacacacaca | cacacacaca | cacaaatgca ggtcaaactg | 120 |
| gtgacgtgtg | agtcagg | | | | 137 |

<210> SEQ ID NO 11
<211> LENGTH: 179
<212> TYPE: DNA
<213> ORGANISM: Rhinoceros unicornis

<400> SEQUENCE: 11

```
gaatgctgat catttagtga caagtgaaaa cacacacaca cacacacaca cacacacaca        60
cacacacaca cacagcgatg ttaaggaaag gtctgtatga cttccaggag gacgttgggt       120
gaaaagagaa ggaagtggaa tcttggacta tgaaaaaatg tgatatctca actggaccc       179
```

<210> SEQ ID NO 12
<211> LENGTH: 208
<212> TYPE: DNA
<213> ORGANISM: Rhinoceros unicornis

<400> SEQUENCE: 12

```
atggtggaag aagtgcagcc ttgtgactgg tgaccacacc agaaagatgc agtgggggag        60
gagaggctct aaaaatggag aacaaaacaa taatggctca ttgtaaagat gaagataggc       120
attcagacta acagcatcac acacacacac acacacacac acactgaatg cacagtatgt       180
gctgagtagg cgctagagac acagaagt                                          208
```

<210> SEQ ID NO 13
<211> LENGTH: 191
<212> TYPE: DNA
<213> ORGANISM: Rhinoceros unicornis

<400> SEQUENCE: 13

```
cttgagcaga gtagaatttg gcatattcaa gaaacagata gaattccatc actgctggaa        60
tatattggag aaaggagtac ctctctctct ctttctctgt ctctctctta cacacacaca       120
cacacataca cacacactcc aatttccctg atacacacag catacgaaat aggaatgagg       180
tggatacaga g                                                            191
```

<210> SEQ ID NO 14
<211> LENGTH: 176
<212> TYPE: DNA
<213> ORGANISM: Rhinoceros unicornis

<400> SEQUENCE: 14

```
cagcacaatg tttggcactt gtaagtgctc tgtaaatgtc aattccctgc cagcctaaca        60
cacacacaca cacacacaca cacacacaca cacacagaca cctgcccect atcgcagcct       120
ttgaattgca ggtgtaagtc tttgtaaata tccttggtgg tgacacaaga ctccaa          176
```

<210> SEQ ID NO 15
<211> LENGTH: 85
<212> TYPE: DNA
<213> ORGANISM: Rhinoceros unicornis

<400> SEQUENCE: 15

```
ctgccttaac gactgaactg cctgattttg tgtgtgtgtg tgtgtgtgtg tatgtatgtg        60
cgtatgtggc atgagataac ctcca                                             85
```

<210> SEQ ID NO 16
<211> LENGTH: 182
<212> TYPE: DNA
<213> ORGANISM: Rhinoceros unicornis

<400> SEQUENCE: 16

-continued

```
gtttatacta tgccctgcac attttaaaaa accctccaca cacagaaaca caacacacac    60
acacacacac acacacacag agagacatgc ttatagcaag taagcagttt tgcagatctc   120
acatttggga atagtgaatg tcttaagttc caaaatttat accaatctat tcagtagcat   180
cc                                                                  182
```

<210> SEQ ID NO 17
<211> LENGTH: 240
<212> TYPE: DNA
<213> ORGANISM: Rhinoceros unicornis

<400> SEQUENCE: 17

```
aggtgattag ggaattgctg ggtcccaacc ccagagtttt tgattcagta ggtctgggtg    60
gggccaaaaa atctgaaaga gtttcagttg ctgggaacag gaggggtgtg tatgtgtgtg   120
tgtatgtgtg tgtgtgtgtg tgtgtgtgtg tgtgtgtgtt agggagatcg gagtaggagg   180
ataagggaag atgcttcttt agatttgaat gttaagaaac gcaatgccag gacagaagaa   240
```

<210> SEQ ID NO 18
<211> LENGTH: 222
<212> TYPE: DNA
<213> ORGANISM: Rhinoceros unicornis

<400> SEQUENCE: 18

```
aaccaacttg taatgagagg gctaccaaac ctttctgtgt gtgtgtgtgt gtgtgtgtgt    60
gtgtgagtgt gtgtgttttc ctttccacca ttccaatatt tttcccccctc gtttcccttc   120 tttctctctt tatgcgaatg taagagaatg tggcttaact tcaactctag tgactgttct   180
ttcccgcaag tgtgtgtgtg cgcgtcttcc ttcctgttca tt                      222
```

<210> SEQ ID NO 19
<211> LENGTH: 150
<212> TYPE: DNA
<213> ORGANISM: Rhinoceros unicornis

<400> SEQUENCE: 19

```
ttcagttcag ttttttgctct gagtattatg ttgcttggaa gaaggaatag gattctccct    60
ctctctctct ctctctctct ctctctatat atatatatat atatatataa agattcaagt   120
aagaatcttt gtagaagaag catggatgag                                    150
```

<210> SEQ ID NO 20
<211> LENGTH: 236
<212> TYPE: DNA
<213> ORGANISM: Rhinoceros unicornis

<400> SEQUENCE: 20

```
acagctagaa tcaccaaaac aagaaggctt atgagaaaaa ttagggttag gagtcaccac    60
tcaaaacctt cagaagtttg taatatatgt ctgtatatac atatatactc aggtgtttta   120
tatatttata tatatatata tatacacact aagatatttt atacacatat aatataataa   180
tacacacaca cacacataca cacacacaca cacacactga gatttatgca gcagga       236
```

<210> SEQ ID NO 21
<211> LENGTH: 201
<212> TYPE: DNA
<213> ORGANISM: Rhinoceros unicornis

<400> SEQUENCE: 21

```
ctagcaaaat ctcaaagagg tttgatccaa ccattcaaat tgtttagtat atacccggt      60 ggttgagcac tgctagaaca cacacacacc cccatacgca aacacacaca cacacacaca    120
cacacacaca cacagattgc tgccaccaaa taaatgagtg gtctccaact atccctgggc    180
ccttggtgat tcccttagta a                                              201
```

<210> SEQ ID NO 22
<211> LENGTH: 172
<212> TYPE: DNA
<213> ORGANISM: Rhinoceros unicornis

<400> SEQUENCE: 22

```
ggcaaaacta agagaacttg tgaaaaacac acacacacac acacacacca aagaaaaaa      60 caaaagcatc tttgcctatt aattgaagtt cttaaagagg aaaaaatagt gccctctcac    120
tgactctcaa gccaatccta tgagttcggg tttccatttc agtttggta tc             172
```

<210> SEQ ID NO 23
<211> LENGTH: 99
<212> TYPE: DNA
<213> ORGANISM: Rhinoceros unicornis

<400> SEQUENCE: 23

```
gatttggaag ctaggcattt cctacggtct tgctatagta aatgtcataa aacccattac      60
ctagaatggg gaatttctgt cattcatgag tatcatggc                             99
```

<210> SEQ ID NO 24
<211> LENGTH: 106
<212> TYPE: DNA
<213> ORGANISM: Rhinoceros unicornis

<400> SEQUENCE: 24

```
gatttggaac ctaggcattt cctatagtct tgtatataaa tatagtgtat gcccataaag      60
cccattagct agatagggaa tttctgtcat tcatgagtat catggc                    106
```

<210> SEQ ID NO 25
<211> LENGTH: 128
<212> TYPE: PRT
<213> ORGANISM: Unknown
<220> FEATURE:
<223> OTHER INFORMATION: Not organism specific

<400> SEQUENCE: 25

Met Thr Gly Ser Cys Cys Gly Ser Ser Phe Ser Ser Arg Ser Leu Gly
1               5                   10                  15

Gly Gly Cys Cys Gln Pro Cys Phe Ser Arg Asp Pro Cys Cys Gly Arg
            20                  25                  30

Pro Val Phe Tyr Arg Thr Thr Val Cys Arg Pro Val Cys Val Pro
        35                  40                  45

Arg Tyr Thr Arg Thr Ile Cys Glu Pro Ser Arg Pro Leu Cys Cys
    50                  55                  60

Asp Pro Cys Ser Leu Gln Glu Gly Cys Cys Arg Pro Ile Thr Cys Cys
65                  70                  75                  80

Pro Thr Ser Cys Thr Ala Val Val Cys Arg Pro Arg Cys Trp Ala Ser
                85                  90                  95

Thr Cys Cys Arg Pro Ile Ser Val Gln Ser Pro Cys Tyr Arg Pro Ser
            100                 105                 110

Cys Cys Gln Pro Ala Pro Cys His Thr Ile Cys Arg Thr Ser His Cys
        115                 120                 125

```
<210> SEQ ID NO 26
<211> LENGTH: 152
<212> TYPE: PRT
<213> ORGANISM: Unknown
<220> FEATURE:
<223> OTHER INFORMATION: Not organism specific

<400> SEQUENCE: 26

Met Ser Tyr Asn Phe Ser Thr Arg Asn Cys Ser Ser Arg Pro Ile Gly
1               5                   10                  15

Gly Arg Cys Thr Val Pro Val Ala Glu Val Ala Ile Pro Ser Thr Gln
            20                  25                  30

Ala Asp Cys Leu Ser Gly Ile Ser Leu Pro Ser Ser Phe Gln Thr Gly
        35                  40                  45

Ser Trp Leu Leu Asn His Cys Gln Glu Thr Cys Cys Glu Pro Thr Val
    50                  55                  60

Cys Gln Pro Thr Cys Tyr Gln Gln Thr Ser Cys Val Ser Arg Pro Gly
65                  70                  75                  80

Gln Val Thr Cys Ser Arg Gln Thr Thr Cys Val Ser Asn Pro Cys Ser
                85                  90                  95

Thr Thr Cys Ser Arg Pro Leu Thr Phe Ile Ser Arg Gly Cys Gln Pro
            100                 105                 110

Gln Val Ser Ile Ser Thr Val Cys Gln Pro Val Gly Gly Ile Ser Thr
        115                 120                 125

Val Cys Gln Pro Ala Cys Gly Val Ser Arg Thr Tyr Gln Gln Ser Cys
    130                 135                 140

Val Ser Ser Cys Arg Arg Ile Cys
145                 150

<210> SEQ ID NO 27
<211> LENGTH: 165
<212> TYPE: PRT
<213> ORGANISM: Unknown
<220> FEATURE:
<223> OTHER INFORMATION: Not organism specific

<400> SEQUENCE: 27

Met Ser Tyr Asn Cys Cys Ser Gly Lys Phe Ser Ser Cys Ser Leu Gly
1               5                   10                  15

Gly Tyr Leu Arg Tyr Pro Arg Ser Ser Cys Gly Ser Ser Tyr Pro Ser
            20                  25                  30

Lys Leu Ile Tyr Arg Thr Asp Leu Cys Ser Pro Ser Thr Cys Gln Leu
        35                  40                  45

Gly Ser Ser Leu Tyr Arg Asn Cys Gln Arg Thr Cys Trp Glu Pro Thr
    50                  55                  60

Arg Tyr Gln Thr Pro Cys Val Val Ser Arg Pro Cys Gln Thr Ser Ser
65                  70                  75                  80

Tyr Gly Leu Arg Thr Ser Thr Leu Arg Ser Pro Cys Trp Thr Thr Tyr
                85                  90                  95

Ala Gly Ser Leu Gly Phe Gly Ser Arg Ser Cys Tyr Ser Leu Gly Cys
            100                 105                 110

Gly Ser Ser Val Phe Lys Pro Leu Gly Tyr Arg Val Cys Gly Phe Pro
        115                 120                 125

Ala Leu Gly Tyr Gly Ser Arg Phe Cys Cys Pro Thr Tyr Phe Pro Ser
    130                 135                 140

Arg Ser Cys Gln Phe Ser Cys Tyr Arg Pro Thr Phe Arg Ser Ala Phe
```

Cys Arg Ser Thr Cys
            165

<210> SEQ ID NO 28
<211> LENGTH: 185
<212> TYPE: PRT
<213> ORGANISM: Unknown
<220> FEATURE:
<223> OTHER INFORMATION: Not organism specific

<400> SEQUENCE: 28

Met Glu Met Asn Gly Asp Lys Val Asp His Ser Lys Lys Ala Ser Ile
1               5                   10                  15

Gln Met Asp Ile Glu Pro Leu Ile His Ser Ser Phe His Cys Asn Ser
            20                  25                  30

Ala Glu Leu Thr Thr Pro Val Asn Met Ser Tyr Ser Cys Cys Ser Gly
        35                  40                  45

Asn Phe Phe Ser Cys Ser Leu Gly Gly Tyr Leu His Tyr Pro Gly Ser
    50                  55                  60

Ser Cys Gly Ser Phe Tyr Pro Ser Asn Leu Val Tyr His Thr Asp Leu
65                  70                  75                  80

Trp Ser Pro Ser Pro Cys Gln Arg Ser Cys Tyr Arg Pro Arg Thr Ser
                85                  90                  95

Ile Arg Cys Ile Ser Cys Trp Pro Thr Tyr Ala Ala Ser Leu Gly Ser
            100                 105                 110

Gly Ser Ser Ser Cys Cys Ser Leu Ser Tyr Gly Ser Arg Ser Cys Tyr
        115                 120                 125

Ser Leu Gly Cys Gly Ser Arg Gly Phe Arg Pro Leu Arg Tyr Gly Val
130                 135                 140

Cys Gly Phe Pro Cys Leu Ser Tyr Gly Ser Arg Phe Cys Arg Pro Ile
145                 150                 155                 160

Tyr Phe Ala Ser Arg Ser Cys Gln Ser Ser Cys Tyr Arg Pro Ala Cys
                165                 170                 175

Arg Ser Ile Phe Tyr Gln Ser Thr Cys
            180                 185

<210> SEQ ID NO 29
<211> LENGTH: 419
<212> TYPE: PRT
<213> ORGANISM: Unknown
<220> FEATURE:
<223> OTHER INFORMATION: Not organism specific

<400> SEQUENCE: 29

Met Ile Ser Thr Cys Ser Pro Ala Ser Ile Lys Asn Cys Pro Arg Pro
1               5                   10                  15

Ser Ser Val Cys Ser Ser Met Ser Cys Arg Pro Glu Leu Cys Leu
            20                  25                  30

Gly Tyr Val Cys Gln Pro Val Thr Cys Met Pro Ser Ile Cys Thr Pro
        35                  40                  45

Thr Thr Tyr Arg Pro Ala Ser Cys Leu Ser Lys Thr Tyr Leu Ser Ser
    50                  55                  60

Ser Cys Arg Pro Ala Ser Gly Ile Ser Ser Leu Gly Thr Cys Ser
65                  70                  75                  80

Trp Tyr Cys Glu Gly Thr Phe Asn Gly Ser Glu Lys Glu Thr Met Gln
                85                  90                  95

```
Phe Leu Asn Asp Arg Leu Ala Ser Tyr Leu Glu Lys Val Arg Gln Leu
                100                 105                 110

Glu Arg Glu Asn Ala Glu Leu Glu Gly Lys Ile Gln Glu Ala Cys Gln
            115                 120                 125

Ala Gln Val Pro Ile Cys Pro Asp Tyr Gln Ser Tyr Phe Arg Thr Ile
        130                 135                 140

Glu Glu Leu Gln Gln Lys Val Leu Cys Thr Lys Ala Glu Asn Ala Arg
145                 150                 155                 160

Met Val Val His Ile Asp Asn Ala Lys Leu Ala Ala Asp Asp Phe Arg
                165                 170                 175

Thr Lys Tyr Glu Thr Glu Leu Ala Met Arg Gln Leu Val Glu Ala Asp
            180                 185                 190

Thr Asn Gly Gln Arg Arg Ile Leu Asp Glu Leu Thr Leu Cys Lys Ala
        195                 200                 205

Asp Leu Glu Ala Gln Val Glu Ser Leu Lys Glu Glu Leu Leu Cys Leu
210                 215                 220

Lys Lys Asp His Glu Glu Val Ser Ala Leu Arg Cys Gln Leu Gly
225                 230                 235                 240

Asp Cys Leu Asn Ile Glu Val Asp Ala Leu Pro Pro Val Asp Leu Asn
                245                 250                 255

Arg Met Leu Glu Glu Met Arg Cys Gln Tyr Glu Ala Val Val Glu Thr
            260                 265                 270

Asn His Arg Asp Val Glu Glu Trp Phe Asn Thr Gln Met Glu Glu Leu
        275                 280                 285

Asn Gln Gln Val Ala Thr Ser Ser Glu Gln Leu Gln Ser Tyr Gln Ser
290                 295                 300

Asp Ile Ile Asp Leu Arg Arg Thr Val Asn Thr Leu Glu Ile Glu Leu
305                 310                 315                 320

Gln Ala Gln His Ser Leu Arg Asp Ser Leu Glu Asn Thr Leu Thr Glu
                325                 330                 335

Thr Glu Ala Arg Tyr Ser Ser Gln Leu Ala Gln Met Gln Gly Leu Ile
            340                 345                 350

Thr Ser Val Glu Ala Gln Leu Ala Glu Ile Arg Cys Asp Leu Glu Arg
        355                 360                 365

Gln Asn Gln Glu Tyr Arg Val Leu Leu Asp Val Lys Ala Arg Leu Glu
370                 375                 380

Gly Glu Ile Asn Thr Tyr Trp Gly Leu Leu Glu Ser Glu Asp Cys Lys
385                 390                 395                 400

Tyr Val Gly Pro Ala Glu Ala Val Gln Arg His Val Cys Glu Gly Trp
                405                 410                 415

Gly Arg Pro

<210> SEQ ID NO 30
<211> LENGTH: 445
<212> TYPE: PRT
<213> ORGANISM: Unknown
<220> FEATURE:
<223> OTHER INFORMATION: Not organism specific

<400> SEQUENCE: 30

Met Ala Thr Thr Ile Arg Gln Phe Thr Ser Ser Ser Ile Lys Gly
1               5                   10                  15

Ser Ser Gly Leu Gly Gly Gly Ser Ser Arg Met Ser Cys Arg Val Ser
            20                  25                  30

Gly Gly Leu Gly Ala Gly Ser Cys Arg Leu Gly Ser Thr Ser Gly Leu
```

```
              35                  40                  45
Gly Ser Ala Leu Gly Ser Ser Tyr Ser Ser Cys Tyr Ser Phe Gly
 50                  55                  60

Ser Gly Gly Gly Tyr Gly Gly Tyr Gly Gly Tyr Gly Gly Gly
 65                  70                  75                  80

Tyr Gly Ser Ser Phe Gly Gly Val Glu Gly Leu Leu Ala Gly Ser Glu
                 85                  90                  95

Lys Ala Thr Met Gln Asn Leu Asn Asp Arg Leu Ala Ser Tyr Leu Asp
                100                 105                 110

Lys Val Arg Ala Leu Glu Glu Ala Asn Ala Glu Leu Glu Val Lys Ile
                115                 120                 125

Arg Asp Trp Tyr Gln Lys Gln Ala Pro Gly Pro Ala Pro Asn Tyr Ser
                130                 135                 140

His Tyr Phe Gln Thr Ile Glu Asp Leu Lys Asn Lys Ile Leu Ala Ala
145                 150                 155                 160

Thr Val Asp Asn Ala Ser Ile Leu Leu Gln Ile Asp Asn Ala Arg Leu
                165                 170                 175

Ala Ala Asp Asp Phe Arg Thr Lys Phe Glu Thr Glu Gln Ala Leu Arg
                180                 185                 190

Leu Ser Val Glu Ala Asp Ile Asn Gly Leu Arg Arg Val Leu Asp Glu
                195                 200                 205

Leu Thr Leu Ala Arg Ala Asp Leu Glu Met Gln Ile Glu Asn Leu Lys
                210                 215                 220

Glu Glu Leu Ala Tyr Met Arg Lys Asn His Glu Glu Glu Met Asn Ala
225                 230                 235                 240

Leu Arg Gly Gln Val Gly Gly Glu Ile Asn Val Glu Met Asp Ala Ala
                245                 250                 255

Pro Gly Val Asp Leu Ser Arg Ile Leu Asn Glu Met Arg Asp Gln Tyr
                260                 265                 270

Glu Lys Ile Ala Glu Lys Asn Arg Lys Asp Ala Glu Asp Trp Phe Phe
                275                 280                 285

Ser Lys Thr Glu Glu Leu Asn Arg Glu Val Ala Thr Asn Ser Glu Leu
                290                 295                 300

Val Gln Ser Gly Lys Ser Glu Ile Ser Glu Leu Arg Arg Thr Leu Gln
305                 310                 315                 320

Ala Leu Glu Ile Glu Leu Gln Ser Gln Leu Ser Met Lys Ala Ser Leu
                325                 330                 335

Glu Gly Ser Leu Ala Glu Thr Glu Asn Arg Tyr Cys Met Gln Leu Ser
                340                 345                 350

Gln Ile Gln Gly Leu Ile Ser Ser Val Glu Glu Gln Leu Ala Gln Leu
                355                 360                 365

Arg Cys Glu Met Glu Gln Gln Asn Gln Glu Tyr Lys Ile Leu Leu Asp
                370                 375                 380

Val Lys Thr Arg Leu Glu Gln Glu Ile Ala Thr Tyr Arg Arg Leu Leu
385                 390                 395                 400

Glu Gly Glu Asp Ala His Leu Thr Gln Tyr Lys Pro Arg Glu Pro Val
                405                 410                 415

Thr Thr Arg Gln Val Arg Thr Ile Val Glu Glu Val Gln Asp Gly Arg
                420                 425                 430

Val Ile Ser Ser Arg Glu Gln Val His Gln Thr Thr His
                435                 440                 445

<210> SEQ ID NO 31
```

<211> LENGTH: 461
<212> TYPE: PRT
<213> ORGANISM: Unknown
<220> FEATURE:
<223> OTHER INFORMATION: Not organism specific

<400> SEQUENCE: 31

```
Met Ala Thr Gln Ile Cys Ser Pro Ile Phe Ser Ser Gly Ser Val Arg
1               5                   10                  15

Gly Leu Cys Gly Thr Ala Gly Gly Ile Thr Arg Val Ser Ser Val Arg
            20                  25                  30

Ser Val Gly Ser Cys Arg Ile Pro Ser Leu Ala Gly Ala Ala Arg Ser
        35                  40                  45

Ala Ser Ser Ile Arg Leu Gly Leu Ser Gly Phe Gly Thr Cys Leu Pro
    50                  55                  60

Ala Ser Cys Leu Ser Thr Gly Cys Tyr Pro Ser Ser Phe Val Gly Ser
65                  70                  75                  80

Gly Ser Trp Phe Cys Glu Gly Thr Phe Asn Gly Asn Glu Lys Glu Thr
                85                  90                  95

Met Gln Phe Leu Asn Asp Arg Leu Ala Asn Tyr Leu Glu Lys Val Arg
            100                 105                 110

Gln Leu Glu Gln Glu Asn Ala Glu Leu Glu Ser Arg Ile Arg Glu Trp
        115                 120                 125

Tyr Glu Ser Gln Ile Pro Tyr Ile Cys Pro Asp Tyr Gln Ser Tyr Phe
    130                 135                 140

Arg Thr Ile Glu Glu Leu Gln Gln Lys Ile Leu Leu Thr Lys Ala Glu
145                 150                 155                 160

Asn Ala Arg Leu Val Leu Gln Ile Asp Asn Ala Lys Leu Ala Ala Asp
                165                 170                 175

Asp Phe Arg Thr Lys Tyr Glu Thr Glu Leu Gly Leu Arg Gln Leu Val
            180                 185                 190

Glu Ala Asp Thr Asn Gly Leu Arg Arg Ile Leu Asp Glu Leu Thr Leu
        195                 200                 205

Cys Lys Ala Asp Leu Glu Met Gln Val Glu Ser Leu Lys Glu Glu Leu
    210                 215                 220

Leu Cys Leu Lys Lys Asn His Glu Glu Glu Val Asn Val Leu Arg Gly
225                 230                 235                 240

Gln Leu Gly Asp Arg Leu Asn Val Glu Val Asp Ala Ala Pro Ser Val
                245                 250                 255

Asp Leu Asn Lys Ile Leu Asp Asp Met Arg Cys Gln Tyr Glu Thr Leu
            260                 265                 270

Val Glu Asn Asn Arg Arg Asp Val Glu Thr Trp Phe Asn Thr Gln Thr
        275                 280                 285

Glu Glu Leu Asn Gln Gln Val Val Ser Ser Gln Leu Gln Ser
    290                 295                 300

Cys Gln Val Glu Ile Ile Glu Leu Arg Arg Thr Val Asn Ala Leu Glu
305                 310                 315                 320

Ile Glu Leu Gln Ala Gln Gln Ser Thr Arg Asn Ser Leu Glu Ser Thr
                325                 330                 335

Leu Ala Glu Thr Glu Ala Arg Tyr Ser Ser Gln Leu Ala Gln Met Gln
            340                 345                 350

Gly Leu Ile Thr Asn Val Glu Ala Gln Leu Ala Glu Ile Arg Cys Asp
        355                 360                 365

Leu Glu Arg Gln Asn His Glu Tyr Gln Val Leu Leu Asp Val Lys Ala
    370                 375                 380
```

```
Arg Leu Glu Ser Glu Ile Ala Thr Tyr Arg Arg Leu Leu Glu Ser Glu
385                 390                 395                 400

Asp Cys Lys Leu Pro Ala His Pro Cys Ala Thr Glu Cys Lys Pro Ala
            405                 410                 415

Ile Arg Val Pro Tyr Val Ser Thr Val Pro Cys Ala Gln Ala Ser Gln
        420                 425                 430

Val Ser Ala Gln Ile Arg Thr Ile Thr Glu Glu Ile Arg Asp Gly Lys
    435                 440                 445

Ile Ile Ser Ser Arg Glu His Leu Gln Pro Cys Pro Leu
450                 455                 460

<210> SEQ ID NO 32
<211> LENGTH: 472
<212> TYPE: PRT
<213> ORGANISM: Unknown
<220> FEATURE:
<223> OTHER INFORMATION: Not organism specific

<400> SEQUENCE: 32

Met Thr Thr Cys Ser Arg Gln Phe Thr Ser Ser Ser Leu Lys Gly
1               5                   10                  15

Ser Tyr Gly Ile Gly Gly Gly Ser Ser Arg Ile Ser Ile Leu Gly
            20                  25                  30

Gly Gly Ser Tyr Gln Ala Pro Ser Ala Tyr Gly Gly Gly Leu Ser Val
        35                  40                  45

Ser Thr Arg Tyr Ser Ser Gly Gly Ala Cys Gly Leu Gly Gly Gly Tyr
    50                  55                  60

Gly Gly Gly Phe Ser Ser Ser Ser Phe Gly Gly Ala Leu Gly Ser
65                  70                  75                  80

Gly Phe Gly Gly Gly Tyr Gly Gly Leu Gly Ala Gly Phe Gly Ala
                85                  90                  95

Gly Phe Gly Gly Gly Phe Ile Gly Gly Asp Gly Gly Leu Ile Ser Gly
            100                 105                 110

Asn Glu Lys Ile Thr Met Gln Asn Leu Asn Asp Arg Leu Ala Ser Tyr
        115                 120                 125

Leu Asp Lys Val Arg Ala Leu Glu Glu Ala Asn Ala Glu Leu Glu Val
    130                 135                 140

Lys Ile Arg Asp Trp Tyr Leu Lys Gln Arg Pro Thr Glu Pro Lys Asp
145                 150                 155                 160

Tyr Ser Pro Tyr Phe Arg Thr Ile Glu Asp Leu Arg Asn Lys Ile Ile
                165                 170                 175

Thr Ala Thr Ile Glu Asn Ala Gln Pro Ile Leu Gln Ile Asp Asn Ala
            180                 185                 190

Arg Leu Ala Ala Asp Asp Phe Arg Thr Lys Tyr Glu His Glu Leu Ala
        195                 200                 205

Leu Arg Gln Ser Val Glu Ala Asp Ile Asn Gly Leu Arg Arg Val Leu
    210                 215                 220

Asp Glu Leu Thr Leu Ala Arg Thr Asp Leu Glu Met Gln Ile Glu Ser
225                 230                 235                 240

Leu Lys Glu Glu Leu Ala Tyr Leu Arg Lys Asn His Gln Asp Glu Met
                245                 250                 255

Asn Ala Leu Arg Gly Gln Thr Gly Gly Asp Val Asn Val Glu Met Asp
            260                 265                 270

Ala Ala Pro Ser Val Asp Leu Ser Arg Ile Leu Asn Glu Met Arg Asp
        275                 280                 285
```

Gln Tyr Glu Gln Ile Ala Glu Lys Asn Arg Arg Asp Ala Glu Ala Trp
            290                 295                 300

Phe Leu Arg Lys Thr Glu Leu Asn Lys Glu Val Ala Ser Asn Ser
305                 310                 315                 320

Glu Leu Val Gln Thr Ser Arg Ser Glu Val Thr Glu Leu Arg Arg Val
                325                 330                 335

Leu Gln Gly Leu Glu Ile Glu Leu Gln Ser Gln Leu Ser Leu Lys Ala
            340                 345                 350

Ser Leu Glu Asn Ser Leu Glu Glu Thr Lys Gly Arg Tyr Cys Met Gln
            355                 360                 365

Leu Ala Gln Ile Gln Gly Leu Ile Ser Val Glu Glu Gln Leu Ala
            370                 375                 380

Gln Leu Arg Cys Glu Met Glu Gln Ser Gln Glu Tyr Gln Ile Leu
385                 390                 395                 400

Leu Asp Val Lys Thr Arg Leu Glu Gln Glu Ile Ala Thr Tyr Arg Arg
                405                 410                 415

Leu Leu Glu Gly Glu Asp Ala His Leu Ser Ser Gln His Thr Ser Ser
            420                 425                 430

Gln Ser Tyr Ser Ser Arg Asp Val Ile Ser Ser Ser Ser Thr Ser
            435                 440                 445

Ser Ser Arg Gln Thr Arg Ser Ile Leu Lys Glu Gly Ser Ser Ser Phe
450                 455                 460

Ser Gln Gly Gln Asn Ser Lys Pro
465                 470

<210> SEQ ID NO 33
<211> LENGTH: 478
<212> TYPE: PRT
<213> ORGANISM: Unknown
<220> FEATURE:
<223> OTHER INFORMATION: Not organism specific

<400> SEQUENCE: 33

Met Thr Thr Cys Ser Arg Gln Phe Thr Ser Ser Ser Ser Leu Lys Gly
1               5                   10                  15

Ser Cys Gly Ile Gly Gly Gly Ser Ser Arg Ile Ser Ser Val Leu Gly
            20                  25                  30

Gly Gly Ser Tyr Arg Ala Pro Ser Ala Tyr Gly Gly Gly Leu Ser Val
        35                  40                  45

Ser Thr Arg Tyr Ser Ser Gly Gly Ala Cys Gly Leu Gly Gly Gly Tyr
    50                  55                  60

Gly Gly Gly Phe Ser Ser Ser Ser Phe Gly Gly Ala Leu Gly Ser
65                  70                  75                  80

Ser Tyr Gly Gly Tyr Gly Gly Leu Gly Ala Gly Leu Gly Gly
            85                  90                  95

Gly Phe Gly Gly Gly Ile Gly Gly Phe Gly Gly Phe Gly Gly
                100                 105                 110

Gly Asp Gly Leu Leu Val Gly Ser Glu Lys Val Thr Met Gln Asn Leu
            115                 120                 125

Asn Asp Arg Leu Ala Ser Tyr Leu Asp Lys Val Arg Ala Leu Glu Glu
        130                 135                 140

Ala Asn Ala Asp Leu Glu Val Lys Ile Arg Asp Trp Tyr Gln Lys Gln
145                 150                 155                 160

Arg Pro Ala Glu Ile Lys Asp Tyr Ser Pro Tyr Phe Lys Thr Ile Glu
                165                 170                 175

```
Asp Leu Arg Asn Lys Ile Leu Thr Ala Thr Val Asp Asn Ala Asn Val
            180                 185                 190

Val Leu Gln Ile Asp Asn Ala Arg Leu Ala Ala Asp Phe Arg Thr
        195                 200                 205

Lys Tyr Glu Thr Glu Leu Asn Leu Arg Leu Ser Val Glu Ala Asp Ile
            210                 215                 220

Asn Gly Leu Arg Arg Val Leu Asp Glu Leu Thr Leu Ala Arg Thr Asp
225                 230                 235                 240

Leu Glu Met Gln Ile Glu Ser Leu Lys Glu Leu Ala Tyr Leu Arg
                245                 250                 255

Lys Asn His Glu Glu Met Asn Ser Leu Arg Gly Gln Val Gly Gly
            260                 265                 270

Asp Val Asn Val Glu Met Asp Ala Ala Pro Gly Val Asp Leu Ser Arg
            275                 280                 285

Ile Leu Asn Glu Met Arg Asp Gln Tyr Glu Lys Ile Ala Glu Lys Asn
            290                 295                 300

Arg Lys Asp Ala Glu Asp Trp Phe Phe Ser Lys Thr Glu Glu Leu Asn
305                 310                 315                 320

Arg Glu Val Ala Thr Asn Ser Glu Leu Val Gln Ser Gly Lys Ser Glu
                325                 330                 335

Ile Ser Glu Leu Arg Arg Thr Val Gln Asn Leu Glu Ile Glu Leu Gln
            340                 345                 350

Ser Gln Leu Ser Met Lys Ala Ser Leu Glu Asn Ser Leu Glu Glu Thr
            355                 360                 365

Lys Gly Arg Tyr Cys Met Gln Leu Ala Gln Ile Gln Glu Leu Ile Ser
            370                 375                 380

Ser Val Glu Glu Gln Leu Ala Gln Leu Arg Cys Glu Met Glu Gln Gln
385                 390                 395                 400

Asn Gln Glu Tyr Lys Ile Leu Leu Asp Val Lys Thr Arg Leu Glu Gln
                405                 410                 415

Glu Ile Ala Thr Tyr Arg Arg Leu Leu Glu Gly Glu Asp Ala His Leu
            420                 425                 430

Ser Ser Ser Gln Phe Ser Ser Gly Ser Gln Ser Ser Arg Asp Val Thr
            435                 440                 445

Ser Ser Ser Arg Gln Ile Arg Thr Lys Ile Met Asp Val His Asp Gly
            450                 455                 460

Lys Val Val Ser Thr His Glu Gln Val Leu Arg Thr Lys Asn
465                 470                 475

<210> SEQ ID NO 34
<211> LENGTH: 486
<212> TYPE: PRT
<213> ORGANISM: Unknown
<220> FEATURE:
<223> OTHER INFORMATION: Not organism specific

<400> SEQUENCE: 34

Met Thr Cys Gly Ser Tyr Cys Ala Gly Arg Ala Phe Ser Cys Ala Ser
1               5                   10                  15

Ala Cys Gly Pro Arg Pro Gly Arg Cys Cys Ile Thr Ala Ala Pro Tyr
            20                  25                  30

Arg Gly Val Ser Cys Tyr Arg Gly Leu Ser Gly Gly Phe Gly Ser Arg
        35                  40                  45

Ser Leu Cys Gly Gly Phe Arg Ala Gly Ser Cys Gly Arg Ser Phe Gly
    50                  55                  60
```

```
Tyr Arg Ser Gly Gly Val Arg Gly Pro Ser Ala Pro Cys Ile Thr Thr
 65                  70                  75                  80

Val Ser Val Asn Glu Ser Leu Leu Ala Pro Leu Asn Leu Glu Ile Asp
                 85                  90                  95

Pro Asn Ala Gln Tyr Val Lys Gln Glu Lys Glu Gln Ile Lys Ser
            100                 105                 110

Leu Asn Asn Arg Phe Ala Ala Phe Ile Asp Lys Val Arg Phe Leu Glu
            115                 120                 125

Gln Gln Asn Lys Leu Leu Glu Thr Lys Leu Gln Phe Tyr Gln Asn Arg
            130                 135                 140

Lys Cys Cys Glu Ser Asn Leu Glu Pro Leu Phe Ser Gly Tyr Leu Glu
145                 150                 155                 160

Thr Leu Arg Arg Glu Ala Glu Arg Val Glu Ala Asp Ser Gly Arg Leu
                165                 170                 175

Ala Ser Glu Leu Asn His Val Gln Glu Val Leu Glu Gly Tyr Lys Lys
            180                 185                 190

Arg Tyr Glu Glu Glu Val Ser Leu Arg Ala Thr Ala Glu Asn Glu Phe
            195                 200                 205

Val Ala Leu Lys Lys Asp Val Asp Cys Ala Tyr Leu Gln Lys Ser Asp
210                 215                 220

Leu Glu Ala Asn Ala Glu Ala Leu Thr Gln Glu Val Asp Phe Leu Arg
225                 230                 235                 240

Arg Leu Tyr Glu Glu Glu Ile Arg Val Leu Gln Ala His Ile Ser Asp
                245                 250                 255

Thr Ser Val Ile Val Lys Met Asp Asn Ser Arg Asp Leu Asn Leu Asp
            260                 265                 270

Ser Ile Val Ala Glu Ile Lys Ala His Tyr Asp Asp Ile Ala Ser Arg
            275                 280                 285

Ser Arg Ala Glu Ala Glu Ser Trp Tyr Arg Thr Lys Cys Glu Glu Ile
            290                 295                 300

Lys Ala Thr Val Val Arg His Gly Glu Thr Leu Arg Arg Thr Lys Glu
305                 310                 315                 320

Glu Ile Asn Glu Leu Asn Arg Leu Ile Gln Arg Leu Thr Ala Glu Ile
                325                 330                 335

Glu Asn Ala Lys Cys Gln Asn Ser Lys Leu Glu Ala Ala Val Ala Glu
            340                 345                 350

Ala Glu Gln Gln Gly Glu Ala Ala Leu Ser Asp Ala Arg Ser Lys Leu
            355                 360                 365

Ala Gly Leu Glu Gly Ala Leu Gln Lys Ala Lys Gln Asp Met Ala Cys
            370                 375                 380

Leu Leu Arg Glu Tyr Gln Glu Val Leu Asn Ser Lys Leu Gly Leu Asp
385                 390                 395                 400

Ile Glu Ile Ala Thr Tyr Arg Arg Leu Leu Glu Gly Glu Glu Gln Arg
                405                 410                 415

Leu Cys Glu Gly Val Gly Ser Val Asn Val Cys Val Ser Ser Ser Arg
            420                 425                 430

Gly Gly Ile Val Cys Gly Asp Leu Cys Ala Ser Gly Ala Ala Pro Ala
            435                 440                 445

Val Thr Thr Ser Val Cys Ser Ala Pro Cys Ser Gly Asn Val Val Val
            450                 455                 460

Gly Thr Ala Asn Ala Cys Ala Pro Cys Thr Leu Gly Cys Lys Arg Cys
465                 470                 475                 480
```

His His His His His His
              485

<210> SEQ ID NO 35
<211> LENGTH: 491
<212> TYPE: PRT
<213> ORGANISM: Unknown
<220> FEATURE:
<223> OTHER INFORMATION: Not organism specific

<400> SEQUENCE: 35

Met Thr Cys Gly Phe Ser Ser Val Gly Cys Gly Phe Ser Pro Arg Thr
1               5                   10                  15

Phe Ser Cys Ala Ser Ala Cys Gly Pro Arg Pro Gly Arg Cys Cys Ile
            20                  25                  30

Thr Ala Ala Pro Tyr Arg Gly Val Ser Cys Tyr Arg Gly Leu Ser Gly
        35                  40                  45

Gly Phe Gly Ser Arg Ser Leu Cys Gly Gly Phe Arg Ala Gly Ser Cys
    50                  55                  60

Gly Arg Ser Phe Gly Tyr Arg Ser Gly Gly Ile Cys Gly Pro Ser Ala
65                  70                  75                  80

Pro Cys Ile Thr Thr Val Ser Val Asn Glu Ser Leu Leu Ala Pro Leu
                85                  90                  95

Asn Leu Glu Ile Asp Pro Asn Ala Gln Cys Val Lys His Glu Glu Lys
            100                 105                 110

Glu Gln Ile Lys Ser Leu Asn Asn Arg Phe Thr Ala Phe Ile Asp Lys
        115                 120                 125

Val Arg Phe Leu Glu Gln Gln Asn Lys Leu Leu Glu Thr Lys Leu Gln
    130                 135                 140

Phe Tyr Gln Asn Arg Lys Cys Cys Asp Ser Asn Leu Glu Leu Leu Phe
145                 150                 155                 160

Ser Gly Tyr Leu Glu Thr Leu Arg Arg Glu Ala Glu Cys Val Glu Ala
                165                 170                 175

Asp Ser Gly Arg Leu Ala Ser Glu Leu Asn His Val Gln Glu Val Leu
            180                 185                 190

Glu Gly Tyr Lys Lys Arg Tyr Glu Glu Val Thr Leu Arg Thr Thr
        195                 200                 205

Ala Glu Asn Glu Phe Val Ala Leu Lys Lys Asp Met Asp Cys Ala Tyr
    210                 215                 220

Leu Arg Lys Ser Asp Leu Glu Ala Asn Ala Glu Ala Leu Thr Gln Glu
225                 230                 235                 240

Val Asp Phe Leu Arg Arg Leu Tyr Glu Glu Ile His Val Leu Gln
                245                 250                 255

Ala Asn Ile Ser Asp Thr Ser Val Ile Val Lys Met Asp Asn Ser Arg
            260                 265                 270

Asp Leu Asn Leu Asp Ser Ile Val Ala Glu Ile Lys Ala Gln Tyr Asp
        275                 280                 285

Asp Met Ala Ser Arg Ser Gln Ala Glu Ala Glu Ser Trp Tyr Cys Thr
    290                 295                 300

Lys Cys Glu Glu Ile Lys Ala Thr Val Val Arg His Gly Glu Thr Leu
305                 310                 315                 320

Arg Arg Thr Lys Glu Glu Ile Asn Glu Leu Asn Arg Leu Ile Gln Arg
                325                 330                 335

Leu Thr Ala Glu Ile Glu Asn Ala Lys Cys Gln Asn Ser Lys Leu Glu
            340                 345                 350

Ala Ala Val Ala Glu Ala Glu Gln Gln Gly Glu Ala Ala Leu Ser Asp
            355                 360                 365

Ala Arg Ser Lys Leu Ala Gly Leu Glu Gly Ala Leu Gln Met Ala Lys
370                 375                 380

Gln Asp Met Ala Cys Leu Leu Arg Glu Tyr Gln Glu Val Leu Asn Ser
385                 390                 395                 400

Lys Leu Gly Leu Asp Ile Glu Ile Ala Thr Tyr Arg Arg Leu Leu Glu
                405                 410                 415

Gly Glu Glu Gln Arg Leu Cys Glu Gly Val Gly Ala Val Asn Val Cys
            420                 425                 430

Val Ser Ser Ser Gln Gly Gly Ile Ile Cys Gly Asp Leu Cys Val Ser
            435                 440                 445

Gly Ser Arg Pro Val Ala Gly Ser Val Cys Ser Ala Pro Cys Gly Gly
            450                 455                 460

Asn Leu Val Val Ser Thr Gly Leu Cys Ala Pro Cys Ser Gln Leu Asn
465                 470                 475                 480

Thr Thr Thr Gly Ser Cys Gly Leu Gly Arg Cys
                485                 490

<210> SEQ ID NO 36
<211> LENGTH: 491
<212> TYPE: PRT
<213> ORGANISM: Unknown
<220> FEATURE:
<223> OTHER INFORMATION: Not organism specific

<400> SEQUENCE: 36

Met Asp Thr Lys Gly Tyr Ile Thr Thr Ile Ser Ser Thr Pro Cys
1               5                   10                  15

Gln Ser Cys Ser Arg Ile Thr Asn Phe Arg Thr Ile Ser Ser Asn Thr
            20                  25                  30

Asn Cys Gln His Gly Gly Leu Lys Ala Asn Ser Cys Gln Pro Thr Gly
        35                  40                  45

His Val Leu Lys Thr Arg Gln Thr Pro Gly Cys Gln His Thr Pro Cys
    50                  55                  60

Leu Cys Leu Thr Pro Ile Cys Leu Ile Ser Asn Phe Asn Ala Cys Pro
65                  70                  75                  80

Ser Ala Asp Asp Cys Gly Trp Gly Gly Glu Gly Ile Asn Ser Asn Glu
                85                  90                  95

Lys Glu Thr Met Gln Val Leu Asn Asp Arg Leu Ala Asn Tyr Leu Glu
            100                 105                 110

Lys Val Arg Met Leu Glu Gln Glu Asn Ala Glu Leu Glu Cys Lys Ile
        115                 120                 125

Gln Glu Glu Ser Asn Lys Glu Leu Pro Val Ile Ser Pro Asp Tyr Leu
    130                 135                 140

Ser Tyr Tyr Ala Thr Ile Glu Glu Leu Gln Gln Lys Ile Leu Cys Thr
145                 150                 155                 160

Lys Ala Glu Asn Ser Arg Leu Val Ser Gln Ile Asp Asn Thr Lys Leu
                165                 170                 175

Ala Ala Asp Asp Leu Arg Ala Lys Tyr Glu Ala Glu Val Ser Leu Arg
            180                 185                 190

Lys Gln Val Glu Ala Asp Ala Asn Gly Val Gln His Ile Leu Asn Ala
        195                 200                 205

Leu Thr Leu Gly Lys Ala Asp Leu Glu Ala Gln Val His Ser Leu Lys
    210                 215                 220

```
Glu Glu Leu Ile Cys Leu Lys Asn Asn His Glu Glu Ile Asn Ser
225                 230                 235                 240

Leu Gln Ser Gln Leu Gly Asp Arg Leu Asn Ile Glu Val Thr Thr Ala
            245                 250                 255

Pro Ser Val Asp Leu Asn Arg Val Leu Gln Glu Met Arg Cys Gln Tyr
                260                 265                 270

Glu Ser Ile Met Glu Thr Asn Ser Arg Asp Val Glu Gln Trp Phe Asn
            275                 280                 285

Thr Gln Thr Glu Glu Leu Asn Gln Gln Val Val Thr Gly Ser Gln Gln
            290                 295                 300

Gln Gln Cys Cys Gln Lys Glu Ile Ile Glu Leu Arg Arg Thr Met Asn
305                 310                 315                 320

Ile Leu Glu Val Glu Leu Gln Ala Gln His Arg Met Arg Asp Ser Gln
                325                 330                 335

Glu Cys Ile Leu Ala Glu Thr Glu Ala Arg Tyr Ala Ala Leu Leu Ala
            340                 345                 350

Gln Ile Gln Arg Leu Ile Asp Asn Leu Glu Ala Gln Leu Ala Glu Ile
            355                 360                 365

Arg Cys Ala Leu Glu Arg Gln Asn Gln Glu Tyr Glu Ile Leu Leu Asp
370                 375                 380

Val Lys Ser Arg Leu Glu Cys Glu Ile Thr Thr Tyr Arg Ser Leu Leu
385                 390                 395                 400

Glu Ser Leu Asp Gly Lys Phe Ala Cys Asn Pro Cys Ala Ile Lys Cys
                405                 410                 415

Glu Pro Ser Thr Cys Thr Phe Ser Lys Ala Arg Ala Lys Glu Cys Thr
            420                 425                 430

Ser Pro Ile Tyr Met Ser Ser Ala Pro Arg Glu Ile Cys Glu Pro Cys
            435                 440                 445

Ser Ala Cys Gly Ala Leu Ser Arg Ile Leu Val Lys Ile Cys Thr Ile
            450                 455                 460

Thr Lys Glu Ile Lys Asp Gly Lys Val Ile Ser Ser His Glu His Val
465                 470                 475                 480

Gln Pro Cys Phe Ile Thr Arg Pro Ala Lys Val
                485                 490

<210> SEQ ID NO 37
<211> LENGTH: 508
<212> TYPE: PRT
<213> ORGANISM: Unknown
<220> FEATURE:
<223> OTHER INFORMATION: Not organism specific

<400> SEQUENCE: 37

Met Ser Cys Arg Ser Tyr Arg Ile Ser Ser Gly Cys Gly Val Thr Arg
1               5                   10                  15

Thr Phe Ser Ser Cys Ser Ala Val Ala Pro Arg Thr Gly Ser Arg Cys
            20                  25                  30

Cys Ile Ser Ala Ala Pro Tyr Arg Gly Val Ser Cys Tyr Arg Gly Leu
        35                  40                  45

Thr Gly Phe Gly Ser Arg Ser Leu Ser Asn Leu Gly Ser Cys Gly Pro
    50                  55                  60

Arg Leu Ala Val Gly Ser Phe Arg Ala Gly Ser Cys Gly Arg Ser Phe
65                  70                  75                  80

Gly Tyr Arg Ser Gly Gly Val Cys Gly Pro Ser Ala Pro Cys Ile Thr
                85                  90                  95
```

```
Thr Val Ser Val Asn Glu Ser Leu Leu Ala Pro Leu Asn Leu Glu Ile
             100                 105                 110

Asp Pro Asn Ala Gln Cys Val Lys Gln Glu Lys Glu Gln Ile Lys
             115                 120                 125

Ser Leu Asn Asn Arg Phe Ala Ala Phe Ile Asp Lys Val Arg Phe Leu
             130                 135                 140

Glu Gln Gln Asn Lys Leu Leu Glu Thr Lys Trp Gln Phe Tyr Gln Asn
145                 150                 155                 160

Gln Arg Cys Cys Glu Ser Asn Leu Glu Pro Leu Phe Ser Gly Tyr Ile
                 165                 170                 175

Glu Thr Leu Arg Arg Glu Ala Glu Cys Val Glu Ala Asp Ser Gly Arg
             180                 185                 190

Leu Ala Ser Glu Leu Asn His Val Gln Glu Val Leu Glu Gly Tyr Lys
             195                 200                 205

Lys Arg Tyr Glu Glu Glu Val Ala Leu Arg Ala Thr Ala Glu Asn Glu
             210                 215                 220

Phe Val Val Leu Lys Lys Asp Val Asp Cys Ala Tyr Leu Arg Lys Ser
225                 230                 235                 240

Asp Leu Glu Ala Asn Val Glu Ala Leu Val Glu Glu Ser Ser Phe Leu
                 245                 250                 255

Lys Arg Leu Tyr Asp Glu Glu Ile Arg Val Leu Gln Ala His Ile Ser
             260                 265                 270

Asp Thr Ser Val Ile Val Lys Met Asp Asn Ser Arg Asp Leu Asn Leu
             275                 280                 285

Asp Ser Ile Val Ala Glu Ile Lys Ala Gln Tyr Asp Asp Ile Ala Ser
             290                 295                 300

Arg Ser Arg Ala Glu Ala Glu Ser Trp Tyr Arg Thr Lys Cys Glu Glu
305                 310                 315                 320

Ile Lys Ala Thr Val Val Arg His Gly Glu Thr Leu Arg Arg Thr Lys
                 325                 330                 335

Glu Glu Ile Asn Glu Leu Asn Arg Leu Ile Gln Arg Leu Thr Ala Glu
             340                 345                 350

Ile Glu Asn Ala Lys Cys Gln Asn Ser Lys Leu Glu Ala Ala Val Ala
             355                 360                 365

Glu Ala Glu Gln Gln Gly Glu Ala Ala Leu Asn Asp Ala Arg Cys Lys
             370                 375                 380

Leu Ala Gly Leu Glu Glu Ala Leu Gln Lys Ala Lys Gln Asp Met Ala
385                 390                 395                 400

Cys Leu Leu Arg Glu Tyr Gln Glu Val Leu Asn Ser Lys Leu Gly Leu
                 405                 410                 415

Asp Ile Glu Ile Ala Thr Tyr Arg Arg Leu Leu Glu Gly Glu Glu Gln
             420                 425                 430

Arg Leu Cys Glu Gly Val Gly Ser Val Asn Val Cys Val Ser Ser Ser
             435                 440                 445

Arg Gly Gly Gly Ile Ser Cys Gly Gly Leu Thr Tyr Ser Thr Thr Pro
             450                 455                 460

Gly Arg Gln Ile Ala Ser Gly Pro Ser Ala Ile Gly Gly Ser Ile Thr
465                 470                 475                 480

Val Met Ala Pro Asp Ala Cys Ala Pro Cys Gln Pro Arg Pro Ser Ser
                 485                 490                 495

Phe Ser Cys Gly Ser Ser Arg Ser Val Arg Phe Ala
                 500                 505
```

<210> SEQ ID NO 38
<211> LENGTH: 566
<212> TYPE: PRT
<213> ORGANISM: Unknown
<220> FEATURE:
<223> OTHER INFORMATION: Not organism specific

<400> SEQUENCE: 38

```
Met Ser Arg Gln Ser Ser Val Ser Phe Arg Thr Gly Ser Arg Ser
1               5                   10                  15

Phe Ser Thr Ala Ser Ala Val Thr Pro Ser Val Ser Arg Thr Ser Phe
                20                  25                  30

Thr Thr Val Ser Arg Ser Gly Gly Gly Gly Gly Phe Gly Arg Val
            35                  40                  45

Ser Leu Gly Gly Ala Cys Gly Val Gly Gly Tyr Gly Ser Arg Ser Leu
    50                  55                  60

Tyr Asn Leu Gly Gly Gly Phe Gly Phe Gly Gly Ala Gly Ser Gly
65              70                  75                  80

Phe Gly Phe Gly Gly Gly Ala Gly Gly Phe Gly Leu Gly Gly Gly
                85                  90                  95

Ala Gly Phe Gly Gly Gly Phe Gly Gly Pro Gly Phe Pro Val Cys Pro
                100                 105                 110

Pro Gly Gly Ile Gln Glu Val Thr Val Asn Gln Ser Leu Leu Thr Pro
            115                 120                 125

Leu Asn Leu Gln Ile Asp Pro Ala Ile Gln Arg Val Arg Thr Glu Glu
    130                 135                 140

Arg Glu Gln Ile Lys Thr Leu Asn Asn Lys Phe Ala Ser Phe Ile Asp
145                 150                 155                 160

Lys Val Arg Phe Leu Glu Gln Gln Asn Lys Val Leu Asp Thr Lys Trp
                165                 170                 175

Thr Leu Leu Gln Glu Gln Gly Thr Lys Thr Val Arg Gln Asn Leu Glu
            180                 185                 190

Pro Leu Phe Glu Gln Tyr Ile Asn Asn Leu Arg Arg Gln Leu Asp Gly
        195                 200                 205

Ile Leu Gly Glu Arg Gly Arg Leu Asp Ser Glu Leu Arg Asn Met Gln
210                 215                 220

Asp Leu Val Glu Asp Phe Lys Asn Lys Tyr Glu Asp Glu Ile Asn Lys
225                 230                 235                 240

Arg Thr Thr Ala Glu Asn Glu Phe Val Met Leu Lys Lys Asp Val Asp
                245                 250                 255

Ala Ala Tyr Met Asn Lys Val Glu Leu Glu Ala Lys Val Asp Ala Leu
            260                 265                 270

Met Asp Glu Ile Asn Phe Met Arg Met Phe Phe Glu Ala Glu Leu Ser
        275                 280                 285

Gln Met Gln Thr His Val Ser Asp Thr Ser Val Ile Leu Ser Met Asp
    290                 295                 300

Asn Asn Arg Ser Leu Asp Leu Asp Ser Ile Ile Ala Glu Val Lys Ala
305                 310                 315                 320

Gln Tyr Glu Glu Ile Ala Asn Arg Ser Arg Thr Glu Ala Glu Ser Trp
                325                 330                 335

Tyr Gln Thr Lys Tyr Glu Glu Leu Gln Gln Thr Ala Gly Arg His Gly
            340                 345                 350

Asp Asp Leu Arg Asn Thr Lys His Glu Ile Ser Glu Met Asn Arg Met
        355                 360                 365

Ile Gln Arg Leu Arg Ala Glu Ile Asp Asn Val Lys Lys Gln Cys Ala
```

```
                370                 375                 380
Asn Leu Gln Ala Ala Ile Ala Asp Ala Glu Gln Arg Gly Glu Leu Ala
385                 390                 395                 400

Leu Lys Asp Ala Arg Asn Lys Leu Ala Glu Leu Glu Asp Ala Leu Gln
                405                 410                 415

Lys Ala Lys Gln Asp Met Ala Arg Leu Leu Arg Glu Tyr Gln Glu Leu
                420                 425                 430

Met Asn Thr Lys Leu Ala Leu Asp Val Glu Ile Ala Thr Tyr Arg Lys
                435                 440                 445

Leu Leu Glu Gly Glu Glu Cys Arg Leu Ser Gly Glu Gly Val Gly Pro
            450                 455                 460

Val Asn Ile Ser Val Val Thr Asn Thr Val Ser Ser Ala Tyr Gly Gly
465                 470                 475                 480

Gly Ser Gly Phe Gly Gly Ser Leu Gly Gly Leu Gly Gly Gly Leu
                485                 490                 495

Gly Gly Gly Leu Gly Gly Gly Ser Gly Gly Gly Tyr Tyr Ser Ser Ser
                500                 505                 510

Ser Gly Gly Val Gly Leu Gly Ser Gly Leu Ser Val Gly Gly Ser Gly
                515                 520                 525

Phe Ser Ala Gly Ser Gly Leu Gly Leu Gly Val Gly Leu Gly Gly Gly
            530                 535                 540

Gly Gly Ser Ser Ser Val Lys Phe Val Ser Thr Thr Ser Ser Ser
545                 550                 555                 560

Arg Lys Ser Phe Lys Ser
                565

<210> SEQ ID NO 39
<211> LENGTH: 583
<212> TYPE: PRT
<213> ORGANISM: Unknown
<220> FEATURE:
<223> OTHER INFORMATION: Not organism specific

<400> SEQUENCE: 39

Met Pro Leu Lys His Tyr Leu Leu Leu Val Gly Phe Gln Ala Trp
1               5                   10                  15

Gly Ala Gly Leu Ala Tyr Tyr Gly Cys Pro Ser Glu Cys Thr Cys Ser
                20                  25                  30

Arg Ala Ser Gln Val Glu Cys Thr Gly Ala Arg Ile Val Ala Val Pro
            35                  40                  45

Thr Pro Leu Pro Trp Asn Ala Met Ser Leu Gln Ile Leu Asn Thr His
    50                  55                  60

Ile Thr Glu Leu Ser Glu Ser Pro Phe Leu Asn Ile Ser Ala Leu Ile
65                  70                  75                  80

Ala Leu Arg Ile Glu Lys Asn Glu Leu Ser His Ile Met Pro Gly Ala
                85                  90                  95

Phe Arg Asn Leu Gly Ser Leu Arg Tyr Leu Ser Leu Ala Asn Asn Lys
                100                 105                 110

Leu Gln Val Leu Pro Ile Gly Leu Phe Gln Gly Leu Asp Asn Leu Glu
            115                 120                 125

Ser Leu Leu Ser Ser Asn Gln Leu Val Gln Ile Gln Pro Ala His
            130                 135                 140

Phe Ser Gln Phe Ser Asn Leu Lys Glu Leu Gln Leu His Gly Asn His
145                 150                 155                 160

Leu Glu Tyr Ile Pro Asp Gly Val Phe Asp His Leu Val Gly Leu Thr
```

```
            165                 170                 175
Lys Leu Asn Leu Gly Lys Asn Ser Leu Thr His Leu Ser Pro Arg Val
                180                 185                 190

Phe Gln His Leu Gly Asn Leu Gln Val Leu Arg Leu Tyr Glu Asn Arg
            195                 200                 205

Leu Ser Asp Ile Pro Met Gly Thr Phe Asp Gly Leu Gly Asn Leu Gln
        210                 215                 220

Glu Leu Ala Leu Gln Gln Asn Gln Ile Gly Met Leu Ser Pro Gly Leu
225                 230                 235                 240

Phe His Asn Asn Arg Asn Leu Gln Lys Leu Tyr Leu Ser Asn Asn His
                245                 250                 255

Ile Ser Gln Leu Pro Leu Gly Ile Phe Thr Gln Leu Pro Gln Leu Asn
            260                 265                 270

Arg Leu Thr Leu Phe Gly Asn Ser Leu Lys Glu Leu Ser Pro Gly Ile
        275                 280                 285

Phe Gly Pro Met Tyr Asn Leu Arg Glu Leu Trp Leu Tyr Asp Asn His
    290                 295                 300

Ile Thr Ser Leu Pro Asp Asn Val Phe Ser Leu His Gln Leu Gln
305                 310                 315                 320

Val Leu Val Leu Ser Arg Asn Gln Ile Ser Phe Ile Ser Pro Gly Ala
                325                 330                 335

Phe Asn Gly Leu Thr Glu Leu Arg Glu Leu Ser Leu His Thr Asn Ala
            340                 345                 350

Leu Gln Glu Leu Asp Gly His Val Phe Arg Met Leu Ala Asn Leu Gln
        355                 360                 365

Asn Ile Ser Leu Gln Asn Asn Arg Leu Arg Gln Leu Pro Gly Asn Ile
    370                 375                 380

Phe Ala Asn Val Asn Gly Leu Met Thr Ile Gln Leu Gln Asn Asn Gln
385                 390                 395                 400

Leu Glu Asn Leu Pro Met Gly Ile Phe Asp His Leu Gly Asn Leu Cys
                405                 410                 415

Glu Leu Gln Leu Tyr Asp Asn Pro Trp Arg Cys Asp Ser Asp Ile Leu
            420                 425                 430

Pro Leu His Asn Trp Leu Leu Leu Asn Lys Pro Arg Leu Arg Ile Asp
        435                 440                 445

Thr Leu Pro Val Cys Phe Ser Pro Ala Asn Val Arg Gly Gln Ser Leu
    450                 455                 460

Ile Ile Ile Asn Ile Asn Ala Ala Phe Pro Ser Val Gln Val Pro Glu
465                 470                 475                 480

Ile Thr Asp Val Pro Ser Lys Pro Glu Thr Pro Arg Tyr Pro Asp Thr
                485                 490                 495

Ser Ser Tyr Pro Asp Thr Thr Ser Ile Ser Ser Thr Thr Glu Phe Ile
            500                 505                 510

Ser Pro Val Asp Tyr Thr Asp Leu Asn Thr Ile Val Thr Thr Asn Ala
        515                 520                 525

His Ser Thr Leu Gly Met Thr Gln Ala Gln Ser Gly Leu Ala Ile Ala
    530                 535                 540

Ala Ile Val Ile Gly Ile Ala Leu Ala Cys Ser Leu Ala Ala Cys
545                 550                 555                 560

Ile Cys Cys Cys Cys Lys Lys Lys Ser His Ala Val Leu Met Gln
                565                 570                 575

Met Lys Ala Pro Asn Glu Cys
            580
```

<210> SEQ ID NO 40
<211> LENGTH: 584
<212> TYPE: PRT
<213> ORGANISM: Unknown
<220> FEATURE:
<223> OTHER INFORMATION: Not organism specific

<400> SEQUENCE: 40

| Met | Ser | Cys | Arg | Ser | Tyr | Arg | Val | Ser | Ser | Gly | His | Arg | Val | Gly | Asn |
|---|---|---|---|---|---|---|---|---|---|---|---|---|---|---|---|
| 1 | | | | 5 | | | | | 10 | | | | | 15 | |

| Phe | Ser | Ser | Cys | Ser | Ala | Gly | Ile | Pro | Arg | Asn | Leu | Asn | Arg | Phe | Arg |
| | | | 20 | | | | | 25 | | | | | 30 | | |

| Ala | Ser | Ser | Val | Ser | Cys | Arg | Ser | Gly | Pro | Ser | Phe | Arg | Gly | Ile | Gly |
| | | 35 | | | | | 40 | | | | | 45 | | | |

| Gly | Phe | Gly | Ser | Arg | Ser | Val | Ile | Thr | Phe | Gly | Ser | Cys | Ser | Pro | Arg |
| | 50 | | | | | 55 | | | | | 60 | | | | |

| Ile | Ala | Ala | Val | Gly | Pro | Arg | Pro | Ile | Arg | Cys | Gly | Val | Gly | Phe | Gly |
| 65 | | | | | 70 | | | | | 75 | | | | | 80 |

| Ala | Gly | Ser | Gly | Met | Ala | Phe | Gly | Phe | Gly | Asp | Gly | Ile | Gly | Ala | Gly |
| | | | | 85 | | | | | 90 | | | | | 95 | |

| Leu | Gly | Phe | Gly | Ala | Gly | Ser | Cys | Leu | Gly | Tyr | Gly | Phe | Gly | Gly | Pro |
| | | | 100 | | | | | 105 | | | | | 110 | | |

| Gly | Phe | Gly | Tyr | Arg | Val | Gly | Gly | Ile | Gly | Val | Pro | Ala | Ala | Ser | Ser |
| | | 115 | | | | | 120 | | | | | 125 | | | |

| Ile | Thr | Pro | Val | Thr | Val | Asn | Gln | Ser | Leu | Leu | Thr | Pro | Leu | Asn | Leu |
| | 130 | | | | | 135 | | | | | 140 | | | | |

| Glu | Ile | Asp | Pro | Asn | Ala | Gln | Arg | Val | Lys | Arg | Asp | Glu | Lys | Glu | Gln |
| 145 | | | | | 150 | | | | | 155 | | | | | 160 |

| Ile | Lys | Thr | Leu | Asn | Asn | Lys | Phe | Ala | Ser | Phe | Ile | Asp | Lys | Val | Arg |
| | | | | 165 | | | | | 170 | | | | | 175 | |

| Phe | Leu | Glu | Gln | Gln | Asn | Lys | Leu | Leu | Glu | Thr | Lys | Trp | Ser | Phe | Leu |
| | | | 180 | | | | | 185 | | | | | 190 | | |

| Gln | Glu | Gln | Lys | Gly | Ala | Arg | Ser | Asn | Leu | Glu | Pro | Leu | Phe | Glu | Asn |
| | | 195 | | | | | 200 | | | | | 205 | | | |

| Tyr | Ile | Thr | Asn | Leu | Gln | Arg | Gln | Leu | Asp | Ile | Ala | Asn | Ser | Glu | Arg |
| | 210 | | | | | 215 | | | | | 220 | | | | |

| Ala | Arg | Leu | Glu | Ala | Glu | Arg | Asn | Gln | Leu | Gln | Asp | Val | Leu | Glu | Gly |
| 225 | | | | | 230 | | | | | 235 | | | | | 240 |

| Phe | Lys | Lys | Lys | Tyr | Glu | Glu | Glu | Val | Val | Phe | Arg | Ala | Asn | Ala | Glu |
| | | | | 245 | | | | | 250 | | | | | 255 | |

| Asn | Glu | Phe | Val | Ala | Leu | Lys | Lys | Asp | Val | Asp | Ala | Ala | Phe | Leu | Asn |
| | | | 260 | | | | | 265 | | | | | 270 | | |

| Lys | Ala | Glu | Leu | Glu | Ala | Asn | Val | Asp | Thr | Leu | Thr | Gln | Glu | Ile | Asp |
| | | 275 | | | | | 280 | | | | | 285 | | | |

| Phe | Leu | Lys | Thr | Leu | Tyr | Ala | Ala | Glu | Ile | Gln | Leu | Leu | Gln | Ser | His |
| | 290 | | | | | 295 | | | | | 300 | | | | |

| Ile | Ser | Glu | Thr | Ser | Val | Ile | Val | Lys | Met | Asp | Asn | Ser | Arg | Asp | Leu |
| 305 | | | | | 310 | | | | | 315 | | | | | 320 |

| Asp | Leu | Asp | Gly | Ile | Ile | Ala | Glu | Val | Arg | Ala | Gln | Tyr | Glu | Glu | Val |
| | | | | 325 | | | | | 330 | | | | | 335 | |

| Ala | Lys | Arg | Ser | Arg | Ala | Asp | Ala | Glu | Ala | Trp | Tyr | Gln | Thr | Lys | Tyr |
| | | | 340 | | | | | 345 | | | | | 350 | | |

| Glu | Glu | Met | Arg | Val | Thr | Ala | Gly | Gln | His | Cys | Asp | Asn | Leu | Arg | Asn |
| | | 355 | | | | | 360 | | | | | 365 | | | |

```
Thr Arg Glu Glu Ile Asn Glu Leu Thr Arg Leu Ile Gln Arg Leu Lys
        370                 375                 380

Ala Glu Ile Glu His Ala Lys Ala Gln Arg Ala Arg Leu Glu Ala Ala
385                 390                 395                 400

Val Ala Glu Ala Glu Gln Gln Gly Glu Ala Ala Leu Asn Asp Ala Lys
                405                 410                 415

Cys Lys Leu Ala Asp Leu Glu Ala Ala Leu Gln Gln Ala Lys Gln Asp
                420                 425                 430

Met Ala Arg Gln Leu Arg Glu Tyr Gln Glu Leu Met Asn Ala Lys Leu
            435                 440                 445

Gly Leu Asp Ile Glu Ile Ala Thr Tyr Arg Arg Leu Leu Glu Gly Glu
        450                 455                 460

Glu Ile Arg Ile Cys Glu Gly Val Gly Pro Val Asn Ile Ser Val Ser
465                 470                 475                 480

Ser Ser Arg Gly Gly Val Val Cys Gly Pro Glu Ser Leu Val Thr Ser
                485                 490                 495

Ser Thr Leu Ser Arg Ser Gly Val Thr Phe Ser Gly Ser Ser Ser Ile
                500                 505                 510

Arg Pro Ser Gly Ala Cys Gly Ser Ser Leu Gly Val Val Ala
            515                 520                 525

Gly Gly Asp Pro Leu Cys Ala Gly Ser Arg Gly Ser Val Leu Val
        530                 535                 540

Gly Glu Ala Cys Ile Pro Ser Val Pro Cys Pro Leu Pro Thr Glu Gly
545                 550                 555                 560

Phe Ser Cys Ser Gly Arg Ser Ser Leu Arg Phe Val Ser
                565                 570                 575

Thr Thr Thr Arg Arg Thr Lys Tyr
            580

<210> SEQ ID NO 41
<211> LENGTH: 589
<212> TYPE: PRT
<213> ORGANISM: Unknown
<220> FEATURE:
<223> OTHER INFORMATION: Not organism specific

<400> SEQUENCE: 41

Met Ser Arg Gln Ser Ser Val Ser Phe Arg Thr Gly Gly Ser Arg Ser
1               5                   10                  15

Phe Ser Thr Ala Ser Ala Val Thr Pro Ser Val Ser Arg Thr Ser Phe
                20                  25                  30

Thr Thr Val Ser Arg Ser Gly Gly Gly Gly Gly Phe Gly Arg Val
            35                  40                  45

Ser Leu Gly Gly Ala Cys Gly Val Gly Gly Tyr Gly Ser Arg Ser Leu
        50                  55                  60

Tyr Asn Leu Gly Gly Ser Lys Arg Ile Ser Ile Ser Ala Ser Gly Gly
65                  70                  75                  80

Gly Phe Arg Asn Arg Phe Gly Ala Gly Ala Gly Gly Phe Gly Phe
                85                  90                  95

Gly Gly Gly Ala Gly Ser Gly Phe Gly Phe Gly Gly Ala Gly Gly
                100                 105                 110

Gly Phe Gly Leu Gly Gly Gly Ala Gly Phe Gly Gly Phe Gly Gly
            115                 120                 125

Pro Gly Phe Pro Val Cys Pro Pro Gly Gly Ile Gln Glu Val Thr Val
        130                 135                 140
```

```
Asn Gln Ser Leu Leu Thr Pro Leu Asn Leu Gln Ile Asp Pro Ala Ile
145                 150                 155                 160

Gln Arg Val Arg Thr Glu Glu Arg Glu Gln Ile Lys Thr Leu Asn Asn
                165                 170                 175

Lys Phe Ala Ser Phe Ile Asp Lys Val Arg Phe Leu Glu Gln Gln Asn
            180                 185                 190

Lys Val Leu Asp Thr Lys Trp Thr Leu Leu Gln Glu Gln Gly Thr Lys
                195                 200                 205

Thr Val Arg Gln Asn Leu Glu Pro Leu Phe Glu Gln Tyr Ile Asn Asn
        210                 215                 220

Leu Arg Arg Gln Leu Asp Gly Ile Leu Gly Glu Arg Gly Arg Leu Asp
225                 230                 235                 240

Ser Glu Leu Arg Asn Met Gln Asp Leu Val Glu Asp Phe Lys Asn Lys
                245                 250                 255

Tyr Glu Asp Glu Ile Asn Lys Arg Thr Thr Ala Glu Asn Glu Phe Val
            260                 265                 270

Met Leu Lys Lys Asp Val Asp Ala Ala Tyr Met Asn Lys Val Glu Leu
        275                 280                 285

Glu Ala Lys Val Asp Ala Leu Met Asp Glu Ile Asn Phe Met Arg Met
290                 295                 300

Phe Phe Glu Ala Glu Leu Ser Gln Met Gln Thr His Val Ser Asp Thr
305                 310                 315                 320

Ser Val Ile Leu Ser Met Asp Asn Asn Arg Ser Leu Asp Leu Asp Ser
                325                 330                 335

Ile Ile Ala Glu Val Lys Ala Gln Tyr Glu Glu Ile Ala Asn Arg Ser
            340                 345                 350

Arg Thr Glu Ala Glu Ser Trp Tyr Gln Thr Lys Tyr Glu Glu Leu Gln
        355                 360                 365

Gln Thr Ala Gly Arg His Gly Asp Asp Leu Arg Asn Thr Lys His Glu
    370                 375                 380

Ile Ser Glu Met Asn Arg Met Ile Gln Arg Leu Arg Ala Glu Ile Asp
385                 390                 395                 400

Asn Val Lys Lys Gln Cys Ala Asn Leu Gln Ala Ala Ile Ala Asp Ala
                405                 410                 415

Glu Gln Arg Gly Glu Leu Ala Leu Lys Asp Ala Arg Asn Lys Leu Ala
            420                 425                 430

Glu Leu Glu Asp Ala Leu Gln Lys Ala Lys Gln Asp Met Ala Arg Leu
        435                 440                 445

Leu Arg Glu Tyr Gln Glu Leu Met Asn Thr Lys Leu Ala Leu Asp Val
    450                 455                 460

Glu Ile Ala Thr Tyr Arg Lys Leu Leu Glu Gly Glu Glu Cys Arg Leu
465                 470                 475                 480

Ser Gly Glu Gly Val Gly Pro Val Asn Ile Ser Val Val Thr Asn Thr
                485                 490                 495

Val Ser Ser Ala Tyr Gly Gly Gly Ser Gly Phe Gly Gly Ser Leu Gly
            500                 505                 510

Gly Gly Leu Gly Gly Gly Leu Gly Gly Gly Leu Gly Gly Gly Ser Gly
        515                 520                 525

Gly Gly Tyr Tyr Ser Ser Ser Gly Gly Val Gly Leu Gly Ser Gly
    530                 535                 540

Leu Ser Val Gly Gly Ser Gly Phe Ser Ala Gly Ser Gly Leu Gly Leu
545                 550                 555                 560
```

-continued

Gly Val Gly Leu Gly Gly Gly Gly Ser Ser Ser Val Lys Phe
                565                 570                 575

Val Ser Thr Thr Ser Ser Arg Lys Ser Phe Lys Ser
            580                 585

<210> SEQ ID NO 42
<211> LENGTH: 614
<212> TYPE: PRT
<213> ORGANISM: Unknown
<220> FEATURE:
<223> OTHER INFORMATION: Not organism specific

<400> SEQUENCE: 42

Met Ser Arg Cys Phe Ser Ser Val Ser Gly Arg Gly Gly Ala Gly
1               5                   10                  15

Phe Ser Ser Gly Ser Ala Gly Val Val Ser Phe Gln Arg Arg Ser Thr
                20                  25                  30

Ser Ser Ser Val Arg Arg Ser Gly Gly Gly Gly Gly Phe Ser Arg
            35                  40                  45

Gly Arg Cys Gly Ala Gly Gly Ala Gly Gly Gly Phe Gly Ser Arg Ser
    50                  55                  60

Leu Val Asn Leu Gly Gly Ser Lys Ser Ile Ser Ile Ser Val Ala Gly
65                  70                  75                  80

Gly Gly Arg Arg Ser Gly Phe Gly Gly Gly Tyr Gly Gly Ser Ser Phe
                85                  90                  95

Gly Gly Gly Gly Tyr Gly Gly Gly Phe Gly Gly Gly Phe Gly Gly Ser
                100                 105                 110

Gly Gly Phe Gly Gly Gly Phe Gly Ser Gly Gly Phe Gly Gly Gly Ile
                115                 120                 125

Gly Ile Gly Gly Gly Phe Gly Gly Gly Phe Gly Gly Gly Gly Phe Gly
                130                 135                 140

Pro Val Cys Pro Pro Gly Gly Ile Gln Glu Val Thr Ile Asn Gln Ser
145                 150                 155                 160

Leu Leu Gln Pro Leu Asn Val Glu Ile Asp Pro Glu Ile Gln Arg Val
                165                 170                 175

Lys Ser Arg Glu Arg Glu Gln Ile Lys Thr Leu Asn Asn Gln Phe Ala
                180                 185                 190

Thr Phe Ile Asp Lys Val Arg Phe Leu Glu Gln Gln Asn Gln Val Leu
                195                 200                 205

Gln Thr Lys Trp Glu Leu Leu Gln Gln Val Asp Thr Ser Thr Arg Thr
                210                 215                 220

Tyr Asn Leu Glu Pro Leu Phe Glu Ser Tyr Ile Asn Thr Leu Arg Arg
225                 230                 235                 240

Gln Val Glu Gln Leu Lys Asn Asp Gln Pro Arg Leu Asp Ser Glu Leu
                245                 250                 255

Lys Asn Val Gln Asp Leu Val Glu Asp Tyr Arg Arg Lys Tyr Glu Glu
                260                 265                 270

Glu Ile Asn Arg Arg Thr Asn Ala Glu Asn Glu Phe Val Thr Ile Lys
                275                 280                 285

Lys Asp Val Asp Ala Ala Tyr Leu Thr Lys Val Asp Leu Gln Ala Lys
                290                 295                 300

Val Asp Asn Leu Arg Gln Glu Ile Glu Phe Leu Thr Ile Leu Tyr Gln
305                 310                 315                 320

Glu Glu Leu Ser Gln Leu Gln Thr His Ile Ser Asp Thr Asn Val Ile
                325                 330                 335

-continued

```
Leu Ser Met Asp Asn Asn Arg Phe Leu Asp Leu Asp Ser Ile Ile Ala
            340                 345                 350

Glu Val Lys Ala Gln Tyr Glu Glu Ile Ala Gln Arg Ser Lys Ala Glu
        355                 360                 365

Ala Glu Ala Leu Tyr Gln Thr Lys Tyr Glu Glu Leu Gln Ile Thr Ala
    370                 375                 380

Gly Lys His Gly Asp Ser Leu Arg Asp Ser Lys Ile Glu Ile Ser Glu
385                 390                 395                 400

Leu Asn Arg Val Ile Gln Arg Leu Arg Ser Glu Ile Asp Ser Val Lys
                405                 410                 415

Lys Gln Ile Ser Ala Leu Gln Gln Ser Ile Ser Asp Ala Glu Gln Arg
            420                 425                 430

Gly Glu Asn Ala Leu Lys Asp Ala Arg Asn Lys Leu Ala Glu Leu Glu
        435                 440                 445

Asp Ala Leu Gln Lys Ala Lys Glu Asp Leu Ala Arg Leu Leu Arg Asp
    450                 455                 460

Tyr Gln Glu Leu Met Ser Thr Lys Leu Ala Leu Asp Leu Glu Ile Ala
465                 470                 475                 480

Thr Tyr Arg Thr Leu Leu Glu Gly Glu Glu Val Arg Met Ser Gly Glu
                485                 490                 495

Cys Ala Pro Asn Val Ser Val Ser Val Ser Thr Ser His Thr Ser Ile
            500                 505                 510

Ser Gly Gly Gly Ile Arg Gly Gly Gly Ala Phe Ser Gly Gly Gly Gly
        515                 520                 525

Gly Gly Tyr Ser Ser Gly Gly Gly Tyr Ser Ser Gly Gly Gly Gly Gly
    530                 535                 540

Gly Tyr Ser Ser Gly Gly Ile Ser Gly Ser Gln Arg Gly Val Ser Gly
545                 550                 555                 560

Gly Gly Gly Gly Ser Thr Gly Gly Trp Ala Ser Gly Gly Gly Gly Ser
                565                 570                 575

Gly Gly Ser Phe Ser Ser Ser Gly Gly Arg Val Ile Ser Ser Gly Gly
            580                 585                 590

Ser Lys Thr Ser Gly Gly Ser Ser Ser Val Lys Phe Val Ser Ser Ser
        595                 600                 605

Tyr Ser Arg Gly Thr Arg
    610
```

<210> SEQ ID NO 43
<211> LENGTH: 868
<212> TYPE: PRT
<213> ORGANISM: Unknown
<220> FEATURE:
<223> OTHER INFORMATION: Not organism specific

<400> SEQUENCE: 43

```
Met Pro Tyr Asn Cys Cys Leu Pro Asn Val Ser Cys Cys Ser Ser Phe
1               5                   10                  15

Ser Ser Arg Pro Cys Val Pro Ser Cys Arg Ser Cys Thr Leu Pro
            20                  25                  30

Gly Ala Cys Asn Ile Pro Ala Asn Val Gly Ser Cys Ser Trp Phe Cys
        35                  40                  45

Glu Gly Ser Phe Asn Ser Asn Glu Lys Glu Thr Met Gln Phe Leu Asn
    50                  55                  60

Asp Arg Leu Ala Ser Tyr Leu Glu Lys Val Arg Gln Leu Glu Arg Asp
65                  70                  75                  80
```

```
Asn Ala Glu Leu Glu Ser Arg Ile Arg Glu Arg Ser Gln Gln Leu Glu
                 85                  90                  95

Pro Gly Val Cys Ala Asn Tyr Gln Ser Tyr Phe Arg Thr Ile Glu Glu
            100                 105                 110

Leu Gln Gln Lys Ile Leu Ser Ala Lys Ser Glu Asn Ala Arg Leu Val
        115                 120                 125

Leu Gln Ile Asp Asn Ala Lys Leu Ala Ser Asp Phe Arg Thr Asn
        130                 135             140

Thr Met Pro Tyr Asn Cys Cys Leu Pro Asn Leu Ser Cys Arg Ser Thr
145                 150                 155                 160

Phe Ser Ala Arg Pro Cys Val Pro Pro Ser Cys Arg Ser Cys Thr Leu
                165                 170                 175

Pro Gly Ala Cys Asn Ile Pro Ala Asn Val Gly Ser Cys Ser Trp Phe
            180                 185                 190

Cys Glu Gly Ser Phe Asn Gly Ser Glu Lys Glu Thr Met Gln Phe Leu
        195                 200                 205

Asn Asp Arg Leu Ala Ser Tyr Leu Glu Lys Val Arg Gln Leu Glu Arg
        210                 215                 220

Glu Asn Ala Glu Leu Glu Ser Arg Ile Arg Glu Arg Ser Gln Gln Gln
225                 230                 235                 240

Glu Pro Glu Val Cys Ala Asn Tyr Gln Ser Tyr Phe Arg Thr Ile Glu
                245                 250                 255

Ala Leu Gln Gln Lys Ile Leu Ser Ser Lys Ala Glu Asn Ala Arg Leu
                260                 265                 270

Val Val Gln Ile Asp Asn Ala Lys Leu Ala Ala Asp Asp Phe Arg Thr
        275                 280                 285

Lys Tyr Glu Thr Glu Leu Gly Leu Arg Gln Leu Val Glu Ser Asp Ile
        290                 295                 300

Asn Gly Leu Arg Arg Ile Leu Asp Glu Leu Thr Leu Cys Arg Ser Asp
305                 310                 315                 320

Leu Glu Ala Gln Val Glu Ser Leu Arg Glu Glu Leu Ile Ser Leu Lys
                325                 330                 335

Gln Asn His Glu Gln Glu Val Asn Ser Leu Arg Ser Gln Leu Gly Asp
            340                 345                 350

Arg Leu Asn Ile Glu Val Asp Ala Ala Pro Thr Val Asp Leu Asn Arg
        355                 360                 365

Val Leu Asn Glu Thr Arg Ser Gln Tyr Glu Ala Leu Val Glu Thr Asn
        370                 375                 380

Arg Arg Asp Val Glu Glu Trp Phe Thr Thr Gln Val Gly Ile Ser Ala
385                 390                 395                 400

Arg Gly Arg Ser Gly Pro Glu Leu Ser Gln Val Gln Gly Leu Ile Thr
                405                 410                 415

Ser Val Glu Ser Gln Leu Ala Glu Ile Arg Ser Asp Leu Glu Arg Gln
        420                 425                 430

Asn Gln Glu Tyr Gln Val Leu Leu Asp Val Arg Ala Arg Leu Glu Ser
        435                 440                 445

Glu Ile Asn Thr Tyr Arg Gly Leu Leu Glu Ser Glu Asp Cys Asn Thr
        450                 455                 460

Met Ser Tyr Asn Cys Cys Leu Pro Asn Leu Ser Cys Arg Ser Ser Phe
465                 470                 475                 480

Ser Ala Arg Pro Cys Met Pro Pro Ser Cys Arg Ser Cys Thr Leu Pro
                485                 490                 495

Gly Ala Cys Asn Ile Pro Ala Asn Val Gly Ser Cys Ser Trp Phe Cys
```

-continued

```
                500                 505                 510
Glu Gly Ser Phe Asn Ser Ser Glu Lys Glu Thr Met Gln Phe Leu Asn
            515                 520                 525

Asp Arg Leu Ala Ser Tyr Leu Glu Lys Val Arg Gln Leu Glu Arg Asp
        530                 535                 540

Asn Ala Glu Leu Glu Ser Arg Ile Arg Glu Arg Ser Gln Gln Gln Glu
545                 550                 555                 560

Pro Glu Val Cys Ala Asn Tyr Gln Ser Tyr Phe Arg Thr Ile Glu Ala
            565                 570                 575

Leu Gln Gln Lys Ile Leu Cys Thr Lys Ser Glu Asn Ala Arg Leu Val
        580                 585                 590

Val Gln Ile Asp Asn Ala Lys Leu Ala Ala Asp Asp Phe Arg Thr Lys
            595                 600                 605

Tyr Glu Thr Glu Leu Gly Leu Arg Gln Leu Val Glu Ser Asp Ile Asn
        610                 615                 620

Gly Leu Arg Arg Ile Leu Asp Glu Leu Thr Leu Cys Lys Ala Asp Leu
625                 630                 635                 640

Glu Ala Gln Val Glu Ser Leu Lys Glu Glu Leu Leu Cys Leu Lys Gln
            645                 650                 655

Asn His Glu Gln Glu Val Asn Thr Leu Arg Ser Gln Leu Gly Asp Arg
        660                 665                 670

Leu Asn Val Glu Val Asp Ala Ala Pro Thr Val Asp Leu Asn Ser Val
        675                 680                 685

Leu Asn Ala Thr Arg Ser Gln Tyr Glu Ala Leu Val Glu Thr Asn Arg
        690                 695                 700

Arg Asp Val Glu Glu Trp Phe Thr Thr Gln Thr Glu Glu Leu Asn Arg
705                 710                 715                 720

Gln Val Val Ser Ser Ser Glu Gln Leu Gln Ser Tyr Gln Ala Glu Ile
            725                 730                 735

Ile Glu Leu Arg Arg Thr Val Asn Ala Leu Glu Val Glu Leu Gln Ala
        740                 745                 750

Gln His Asn Leu Arg Asp Ser Leu Glu Asn Thr Leu Thr Glu Thr Glu
        755                 760                 765

Ala Arg Tyr Ser Ala Gln Leu Ser Gln Val Gln Gly Leu Ile Thr Ser
770                 775                 780

Val Glu Ser Gln Leu Ala Glu Ile Arg Ser Asp Leu Glu Arg Gln Asn
785                 790                 795                 800

Gln Glu Tyr Gln Val Leu Leu Asp Val Arg Ala Arg Leu Glu Ser Glu
            805                 810                 815

Ile Asn Thr Tyr Arg Gly Leu Leu Glu Ser Glu Asp Cys Lys Leu Pro
            820                 825                 830

Cys Asn Pro Cys Ala Thr Thr Asn Ala Cys Asp Lys Ser Ile Gly Ser
        835                 840                 845

Cys Ile Ser Asn Pro Cys Ala Pro Arg Thr Arg Cys Gly Pro Cys Asn
850                 855                 860

Thr Phe Val Cys
865
```